United States Patent [19]

Schnabel et al.

[11] Patent Number: 5,658,854
[45] Date of Patent: Aug. 19, 1997

[54] ACYLATED AMINOPHENYLSULFONYLUREAS; PREPARATION AND USE AS HERBICIDES AND PLANT GROWTH REGULATORS

[75] Inventors: Gerhard Schnabel, Grosswallstadt; Lothar Willms, Hofheim; Klaus Bauer, Hanau; Hermann Bieringer, Eppstein, all of Germany

[73] Assignee: Hoechst Schering AgrEvo GmbH, Berlin, Germany

[21] Appl. No.: 268,274

[22] Filed: Jun. 30, 1994

[30] Foreign Application Priority Data

Jul. 2, 1993 [DE] Germany .................. 43 22 067.3

[51] Int. Cl.⁶ .................. C07D 239/69; A01N 43/54
[52] U.S. Cl. .................. 504/214; 504/215; 544/295; 544/122; 544/123; 544/82; 544/321; 544/323; 544/324; 544/331; 544/332
[58] Field of Search .................. 504/214, 215; 544/321, 323, 332, 82, 122, 123, 295, 324, 331

[56] References Cited

U.S. PATENT DOCUMENTS

| | | | |
|---|---|---|---|
| 4,632,695 | 12/1986 | Schurter et al. | 544/209 |
| 4,664,695 | 5/1987 | Schurter et al. | 544/331 |
| 4,892,946 | 1/1990 | Levitt | 544/321 |
| 4,981,509 | 1/1991 | Hillemann | 544/206 |

FOREIGN PATENT DOCUMENTS

| | | |
|---|---|---|
| 0001515 | 4/1979 | European Pat. Off. . |
| 0116518 | 8/1984 | European Pat. Off. . |
| 42 36 902 | 5/1994 | Germany . |

*Primary Examiner*—John M. Ford
*Attorney, Agent, or Firm*—Curtis, Morris & Safford, P.C.

[57] ABSTRACT

Acylated aminophenylureas, preparation and use as herbicides and plant growth regulators The compounds of the formula I or their salts

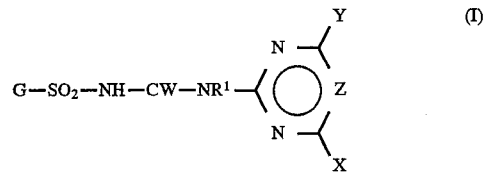

in which G is a radical G1, G2 or G3

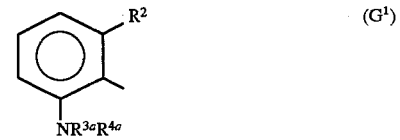

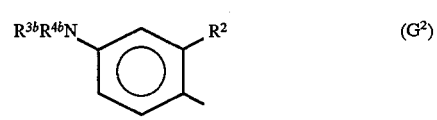

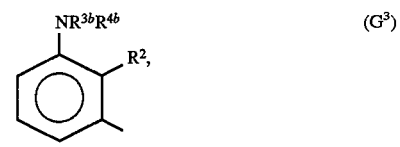

$R^1$ is H or alkyl, $R^2$ is COOH, CSOH or a derivative of the carboxyl or thiocarboxyl group, of 1 to 20 carbon atoms, or acyl of the type CO-R° of 1–12 carbon atoms, or an imino, hydrazone or oxime derivative of the group CO-R°, and R°, $R^{3a}$, $R^{4a}$, $R^{3b}$, $R^{4b}$, W, X, Y and Z are as defined in claim 1, are suitable as selective herbicides and plant growth regulators in crops.

The preparation is carried out in analogy to known processes (see claim 5) by way of intermediates, some of which are new, from the group consisting of benzene-sulfonamides (II), benzenesulfonyl isocyanates (IV) and benzesulfonyl chlorides (VI) and heterocyclically substituted carbamates (III), amines (V) and/or (thio)-isocyanates (XIX).

10 Claims, No Drawings

ACYLATED AMINOPHENYLSULFONYLUREAS; PREPARATION AND USE AS HERBICIDES AND PLANT GROWTH REGULATORS

The invention relates to the technical field of herbicides and plant growth regulators, in particular to that of herbicides for the selective combating of gramineous and broad-leaved weeds in crops.

It is known that heterocyclically substituted phenylsulfonylureas which carry an amino group or a functionalized amino group on the phenyl ring possess herbicidal and plant growth-regulatory properties (EP-A-1515; U.S. Pat. No. 4,892,946; U.S. Pat. No. 4,981,509; EP-A-116 518; U.S. Pat. No. 4,664,695; U.S. Pat. No. 4,632,695).

In addition, German Patent Application P 42 36 902.9 has already proposed phenylsulfonylureas whose phenyl ring has a carboxyl group or derivative thereof in position 2 and an N-alkyl-N-acylamino group in position 5.

Surprisingly it has now also been found that certain heterocyclically substituted phenylsulfonylureas are particularly highly suitable as herbicides or plant growth regulators.

The present invention relates to compounds of the formula (I) and their salts,

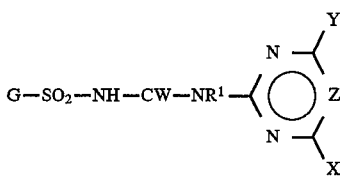

(I)

in which

G is a substituted N-acylaminophenyl radical from the group consisting of $G^1$, $G^2$ and $G^3$

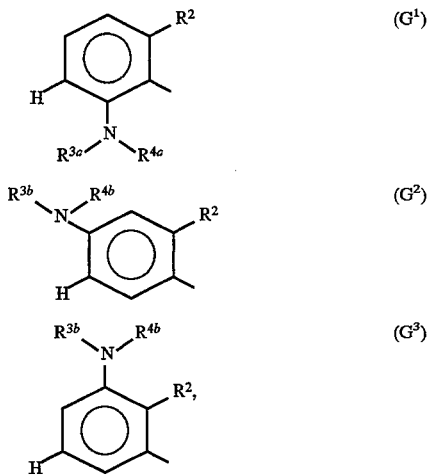

$R^1$ is H or alkyl, $R^2$ is carboxyl, thiocarboxyl or a derivative of the carboxyl or thiocarboxyl group of 1 to 20 carbon atoms, preferably 1 to 12 carbon atoms, or acyl of the type CO-R° of 1 to 12 carbon atoms, in which R° is hydrogen or a saturated or unsaturated and acyclic or cyclic aliphatic radical, or an imine, hydrazone or oxime derivative of the group CO-R°, $R^{3a}$ is hydrogen or a hydrocarbon radical which is unsubstituted or substituted and is of 1 to 18 carbon atoms, preferably 1 to 10 carbon atoms in total, $R^{3b}$ is hydrogen or a hydrocarbon radical which is unsubstituted or substituted and is of 1 to 18 carbon atoms, preferably 1 to 10 carbon atoms in total, $R^{4a}$ is alkylcarbonyl or alkoxycarbonyl of 2 to 12 carbon atoms, the two latter radicals being unsubstituted or substituted by one or more radicals from the group consisting of hydroxyl, amino, substituted sunino, azido, cyano, carboxyl, ($C_1$-$C_4$-alkoxy)carbonyl and ($C_1$-$C_4$-alkyl) thio, -sulfinyl and -sulfonyl, or is aminocarbonyl or aminosulfonyl, the two latter radicals being unsubstituted, N-monosubstituted or N,N-disubstituted, $R^{4b}$ is formyl or aliphatic acyl from the group consisting of CO-R, CS-R, CO-OR, CS-OR and CS-SR of 2 to 12 carbon atoms, R'SO or R'SO$_2$, in which R and R' are each a hydrocarbon radical which is unsubstituted or substituted, for example by one or more radicals from the group consisting of halogen, cyano, azido, carboxyl, alkoxycarbonyl, hydroxyl, amino, mono- and disubstitutedamino, aminocarbonyl, N-mono- and N,N-disubstituted aminocarbonyl, alkoxy, alkylthio, alkylsulfinyl and alkylsulfonyl, or aminocarbonyl or aminosulfonyl, the two latter radicals being unsubstituted, N-monosubstituted or N,N-disubstituted, W is an oxygen or sulfur atom, X and Y independently of one another are hydrogen, halogen, $C_1$-$C_4$-alkyl, $C_1$-$C_4$-alkoxy or $C_1$-$C_4$-alkylthio, the three latter radicals being unsubstituted or substituted by one or more radicals from the group consisting of halogen, $C_1$-$C_4$-alkoxy and $C_1$-$C_4$-alkyl-thio, or mono- or di-($C_1$-$C_4$-alkyl)amino, $C_3$-$C_6$-cycloalkyl, $C_3$-$C_5$-alkenyl, $C_3$-$C_5$-alkenyloxy or $C_3$-$C_5$-alkynyloxy, and Z is CH or N.

In the formula (I) and in the following formulae the radicals alkyl, alkoxy, haloalkyl, haloalkoxy, alkylamino and alkylthio and the corresponding unsaturated and/or substituted radicals in the carbon structure may in each case be straight-chain or branched. If not specifically indicated, the carbon structures of 1 to 4 carbon atoms, or of 2 to 4 carbon atoms in the case of unsaturated groups, are preferred for these radicals. Alkyl radicals, alone and in the composite definitions such as alkoxy, haloalkyl etc., are for example methyl, ethyl, n-propyl or isopropyl, n-butyl, isobutyl, tert-butyl or 2-butyl, pentyls, hexyls, such as n-hexyl, isohexyl and 1,3 -dimethylbutyl, heptyls such as n-heptyl, 1-methylhexyl and 1,4-dimethylpentyl; alkenyl and alkynyl radicals are the possible unsaturated radicals corresponding to the alkyl radicals, alkenyl denoting for example allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl, and alkynyl denoting, for example, propargyl, but-2-yn-1-yl, but-3-yn-1-yl and 1-methylbut-3-yn-1-yl.

An aliphatic radical is a saturated or unsaturated, acyclic or cyclic hydrocarbon radical which may be interrupted by heteroatoms such as O, S and N and may contain further functional groups, for example nitro, cyano, carboxyl, alkylcarbonyl, alkoxycarbonyl, carboxamide, etc.

An unsubstituted or substituted hydrocarbon radical is, for example, alkyl, alkenyl, alkynyl, cycloalkyl, cycloalkenyl, aryl (including heteroaryl) such as phenyl, naphthyl, pyridyl and thienyl, aralkyl such as benzyl, alkylaryl such as tolyl, the abovementioned radicals being unsubstituted or substituted by one or more radicals, for example by radicals from the group consisting of halogen, alkoxy, CN, amino, mono- and dialkylamino, azido, alkylthio, unsubstituted or substituted carboxamido, nitro, alkanoyl, carboxyl, alkoxycarbonyl, alkyl-sulfinyl, alkylsulfonyl and other—preferably low molecular weight—radicals or functional groups which are relatively stable in the relevant compound at room temperature and which are of little or no reactivity under aqueous-neutral conditions.

Substituted aminocarbonyl or aminosulfonyl is, for example, a relevant N-monosubstituted or N,N-disubstituted radical substituted by (if appropriate) different radicals from the group consisting of alkyl, haloalkyl, aryl (including heteroaryl), such as substituted or unsubstituted phenyl, and acyl, for example alkanoyl such as acetyl, and arylcarbonyl such as benzoyl, preferably alkyl.

A heterocyclic radical attached via a nitrogen atom, which may be substituted further, is for example 1-piperidyl, 1-piperazinyl, 4-morpholinyl, 1-pyrrolidinyl, 1-oxa-3-azacyclopent-3-yl, 1-oxa-2-azacyclopent-2-yl, with these radicals possibly being substituted by further radicals, for example alkyl, alkoxy and halogen.

Unsubstituted or substituted phenyl corresponds to unsubstituted phenyl or substituted phenyl, examples of substituents being one or more—preferably 1, 2 or 3—radicals from the group consisting of halogen, alkyl, haloalkyl, alkoxy, haloalkoxy, nitro, cyano, alkoxycarbonyl, alkylcarbonyl, alkanoyl, carbamoyl, mono- and dialkylaminocarbonyl, mono- and dialkylamino, alkylsulfinyl and alkylsufonyl and, in the case of radicals containing carbon atoms, those of 1 to 4 carbon atoms, especially 1 or 2 carbon atoms, being preferred; substituents which are generally preferred are those from the group consisting of halogen, such as fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano; particularly preferred in this context are methyl, methoxy and chlorine.

Halogen is fluorine, chlorine bromine or iodine. Haloalkyl, -alkenyl and -alkynyl are alkyl, alkenyl and alkynyl respectively which are completely or partially substituted by halogen, preferably by fluorine, chlorine and/or bromine and in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is for example $OCF_3$, $OCHF_2$, $OCH_2F$, $CF3CF_2O$, $OCH_2CF_3$ and $OCH_2CH_2Cl$. The same applies to haloalkenyl and other halo-substituted radicals.

The invention also relates to all stereoisomers encompassed by formula (I) and to mixtures thereof. Such compounds of the formula (I) contain one or more asymmetric carbon atoms or else double bonds, which are not indicated separately in the formula (I). The possible stereoisomers defined by their specific spatial form, such as enantiomers, diastereomers and Z and E isomers, are all included in formula (I) and can be obtained from mixtures of the stereoisomers by conventional methods or, alternatively, prepared by stereoselective reactions in combination with the use of stereochemically pure starting materials.

The compounds of the formula (I) are able to form salts in which the hydrogen of the —$SO_2$—NH— group or alternatively other acidic hydrogen atoms (e.g. from COOH etc.) is or are replaced by a cation suitable in agriculture. Examples of these salts are metal salts, especially alkali metal or alkaline earth metal salts, for example sodium salts and potassium salts, or else ammonium salts or salts with organic amines. Salt formation may also take place by the addition of an acid to basic groups, for example amino and alkylamino. Acids suitable for this are strong inorganic and organic acids, for example HCl, BRr, $H_2SO_4$ or $HNO_3$.

Compounds of the formula (I) and their salts according to the invention which are of particular interest are those in which one or more of the following definitions apply for the radicals $R^1$ to Z:

$R^1$ is H or $C_1$–$C_3$-alkyl, $R^2$ is CO-$OR^5$, CS-$SR^6$, CO-$SR^7$, CS-$OR^8$, CO-$R^9$, CO-$NR^{10}R^{11}$, CO-O-N=$CR^{12}R^{13}$, C(=$NR^{14}$) $R^{15}$ or CS-$NR^{16}R^{17}$, $R^{3a}$ is H, $C_1$–$C_5$-alkyl, $C_2$–$C_5$-alkenyl or $C_2$–$C_5$-alkynyl, the three latter radicals being unsubstituted or substituted by one or more radicals from the group consisting of halogen, $C_1$–$C_4$-alkoxy, CN, di-($C_1$–$C_4$-alkyl)amino, $N_s$, and $C_1$–$C_3$-alkylthio, $R^{3b}$ is H, $C_1$–$C_5$-alkyl, $C_3$–$C_6$-cycloalkyl, $C_2$–$C_5$-alkenyl or $C_2$–$C_5$-alkynyl, the four latter radicals being unsubstituted or substituted by one or more radicals from the group consisting of halogen, $C_1$–$C_4$-alkoxy, CN, di- ($C_1$–$C_4$-alkyl) amino, $N_3$ and $C_1$–$C_3$ -alkylthio, $R^{4a}$ is CO- ($C_1$–$C_5$-alkyl) or $CO_2$- ($C_1$–$C_5$-alkyl), the two latter radicals being unsubstituted or substituted by one or more radicals from the group consisting of OH, $NR^{18}R^{19}$, $N_3$, CN, $CO_2H$, $S(O)_x$-($C_1$–$C_4$-alkyl) and $CO_2$- ($C_1$–$C_3$-alkyl), or aminocarbonyl or aminosulfonyl, the two latter radicals being unsubstituted or N-substituted by identical or different radicals from the group consisting of $C_1$–$C_4$-alkyl and $C_1$–$C_4$-haloalkyl, $R^{4b}$ is CHO, CO- ($C_1$–$C_5$-alkyl), CO-($C_3$–$C_6$-cycloalkyl), $CO_2$-($C_1$–$C_5$-alkyl), CO- ($C_2$–$C_5$-alkenyl), CS-($C_1$–$C_5$-alkyl), CO-($C_2$–$C_5$-alkynyl), CO-S-($C_1$–$C_6$-alkyl), CS-O-($C_1$–$C_6$-alkyl) or CS-S-($C_1$–$C_6$-alkyl), the nine latter radicals being unsubstituted or substituted by one or more radicals from the group consisting of halogen, CN, $N_3$, $CO_2H$, $CO_2$-($C_1$–$C_3$-alkyl), OH, $NR^{20}R^{21}$, $S(O)_x$-($C_1$–$C_4$-alkyl), CO-$NR^{22}R^{23}$ and $C_1$–$C_3$-alkoxy, or CO-NR24R25, CS-$^{NR26}R^{27}$, $SO_2R^{28}$ or $SO_2NR^{29}R^{30}$, $R^5$ is $C_1$–$C_5$-alkyl, $C_2$–$C_5$-alkenyl, $C_2$–$C_5$-alkynyl, $C_3$–$C_6$-cycloalkyl or $C_4$–$C_7$-cycloalkylalkyl, the latter five radicals being unsubstituted or substituted by one or more radicals from the group consisting of halogen, CN, $N_3$, $C_1$–$C_3$-alkoxy, $C_1$–$C_3$ -alkylthio, amino, mono- and di-($C_1$–$C_4$-alkyl)amino, $NO_2$, SCN, $C_1$-$C_3$-haloalkoxy and $C_1$–$C_3$-haloalkylthio, $R^6$ is a radical as for $R^5$, $R^7$ is a radical as for $R^5$, $R^8$ is a radical as for $R^5$, $R^9$ is H, $C_1$–$C_6$-alkyl, $C_2$–$C_6$-alkenyl, $C_2$–$C_6$-alkynyl, $C_3$-$C_7$-cycloalkyl, the four latter radicals independently of one another being unsubstituted or substituted by one or more radicals from the group consisting of halogen, $C_1$–$C_4$-alkoxy, $C_1$–$C_4$-alkylthio, $C_1$–$C_4$-halo-alkoxy, $C_1$–$C_4$-haloalkylthio and CN, $R^{10}$ is H, $C_1$–$C_6$-alkyl, $C_2$–$C_6$-alkenyl, $C_2$–$C_6$-alkynyl, the three latter radicals being unsubstituted or substituted by one or more radicals from the group consisting of $C_1$–$C_5$-alkoxy, $C_1$–$C_3$-alkylthio, halogen, CN, amino, $C_1$–$C_4$-alkylamino and di- ($C_1$–$C_4$-alkyl) -amino, or $C_1$–$C_4$-alkoxy or OH, $R^{11}$ is H, $C_1$–$C_6$-alkyl, $C_2$–$C_6$-alkenyl, $C_2$–$C_6$-alkynyl, the three latter radicals being unsubstituted or substituted by one or more radicals from the group consisting of halogen, CN, $NH_2$, mono- and di-($C_1$–$C_4$-alkyl) amino, $C_1$–$C_3$-alkoxy and $C_1$–$C_3$-alkylthio, or $NR^{10}R^{11}$ together is a heterocyclic ring which in addition to the ring nitrogen atom may also contain up to two ring heteroatoms from the group consisting of N, O and S and may be further substituted, $R^{12}$ and $R^{13}$ independently of one another are H, $C_1$–$C_4$-alkyl, $C_2$–$C_4$-alkenyl or $C_2$–$C_4$-alkynyl, or $R^{12}$ and $R^{13}$ together are Am alkylene chain of 3 or 4 carbon atoms, which may also be substituted by $C_1$–$C_4$-alkyl or $C_1$–$C_4$-alkoxy, $R^{14}$ is H, OH, $NH_2$, $NHR^{31}$, $NR^{31}_2$, $C_1$–$C_4$alkyl, $C_1$–$C_4$-alkoxy, $C_2$–$C_4$-alkenyl or $C_2$–$C_4$-alkynyl, the four latter radicals being unsubstituted or substituted by one or more radicals from the group consisting of halogen, $C_1$-$C_3$-alkoxy and $C_1$-$C_3$-alkylthio, $R^{15}$ is H, $C_1$-$C_6$-alkyl, $C_1$-$C_6$-alkoxy, $C_2$-$C_6$-alkenyl, $C_2$-$C_6$-alkynyl, the four latter radicals being unsubstituted or substituted by one or more radicals from the group consisting of halogen, $C_1$-$C_3$-alkoxy and $C_1$-$C_3$-alkylthio, $R^{16}$ is a radical as for $R^{10}$, $R^{17}$ is a radical as for $R^{11}$, $R^{18}$ independently of $R^{19}$ is H, $C_1$-$C_4$-alkyl, $C_2$-$C_5$-alkenyl or $C_2$-$C_5$-alkynyl, the three latter radicals being unsubstituted or substituted by one or more radicals from the group consisting of halogen, $C_1$-$C_3$-alkoxy, $C_1$-$C_3$-alkylthio and CN, $R^{19}$ independently of $R^{18}$ is a radical as for $R^{18}$ or is $C_1$-$C_3$-alkoxy or OH, or $NR^{18}R^{19}$ together is a heterocyclic ring which may in addition to the ring nitrogen atom contain up to two ring heteroatoms from the group consisting of N, O and S and may be further substituted, for example a group of the formulae K1 to K5,

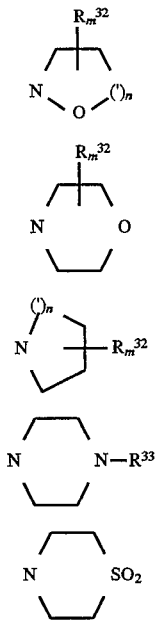

$R^{20}$ independently of $R^{21}$ is H, $C_1$-$C_4$-alkyl, $C_2$-$C_4$-alkenyl or $C_2$-$C_4$-alkynyl, the three latter radicals being unsubstituted or substituted by one or more radicals from the group consisting of halogen, CN, $NH_2$, mono- and di($C_1$-$C_4$) alkylamino, $C_1$-$C_3$-alkoxy, $C_1$-$C_3$-alkylthio and $CO_2$-($C_1$-$C_3$-alkyl), $R^{21}$ independently of $R^{20}$ is a radical as for $R^{20}$ or is CHO, CO-($C_1$-$C_5$-alkyl) or $CO_2$-($C_1$-$C_5$-alkyl) or $NR^{20}R^{21}$ is a heterocyclic ring analogous to $NR^{18}R^{19}$, $R^{22}$ and $R^{23}$ independently of one another are H, $C_1$-$C_3$-alkyl, $C_2$-$C_4$-alkenyl or $C_2$-$C_4$-alkynyl or $NR^{22}R^{23}$ is a heterocyclic ring analogous to $NR^{18}R^{19}$, $R^{24}$ independently of $R^{25}$ is H, $C_1$-$C_4$-alkyl, $C_2$-$C_5$-alkenyl, $C_2$-$C_5$-alkynyl, the three latter radicals being unsubstituted or substituted by one or more radicals from the group consisting of halogen, $C_1$-$C_3$-alkoxy, $C_1$-$C_3$-alkylthio and CN, $R^{25}$ independently of $R^{24}$ is H, $C_1$-$C_4$-alkyl, $C_2$-$C_5$-alkenyl or $C_2$-$C_5$-alkynyl, the three latter radicals being unsubstituted or substituted by one or more radicals from the group consisting of halogen, $C_1$-$C_3$-alkoxy, $C_1$-$C_3$-alkylthio and CN, or is $C_1$-$C_3$-alkoxy or OH, or $NR^{24}R^{25}$ is a heterocyclic ring analogous to $NR^{18}R^{19}$, $R^{26}$ independently of $R^{27}$ is a radical as for $R^{24}$, $R^{27}$ independently of $R^{26}$ is a radical as for $R^{26}$ or is $C_1$-$C_3$-alkoxy or OH, or $NR^{26}R^{27}$ is a heterocyclic ring analogous to $NR^{18}R^{19}$, $R^{28}$ is $C_1$-$C_5$-alkyl, $C_2$-$C_5$-alkenyl or $C_2$-$C_5$-alkynyl, the three latter radicals being unsubstituted or substituted by one or more radicals from the group consisting of halogen, CN, $C_1$-$C_3$-alkoxy and $C_1$-$C_3$-alkylmercapto, $R^{29}$ independently of $R^{30}$ is a radical as for $R^{24}$, $R^{30}$ independently of $R^{29}$ is a radical as for $R^{25}$ or $NR^{29}R^{30}$ is a heterocyclic ring analogous to $NR^{18}R^{19}$, $R^{31}$ is $C_1$-$C_4$-alkyl, $C_2$-$C_4$-alkenyl or $C_2$-$C_4$-alkynyl, the three latter radicals independently of one another being unsubstituted or substituted by one or more radicals from the group consisting of halogen, $C_1$-$C_4$-alkoxy and $C_1$-$C_4$-alkylthiol, $R^{32}$ is H, $C_1$-$C_3$-alkyl, $C_1$-$C_3$-haloalkyl, $C_1$-$C_3$-alkoxyalkyl, halogen or CN, $R^{33}$ is H, $C_1$-$C_3$-alkyl, $C_2$-$C_4$-alkenyl or $C_2$-$C_4$-alkynyl, the three latter radicals being unsubstituted or substituted by a radical from the group consisting of halogen, $C_1$-$C_4$-alkoxy, CN and $C_1$-$C_4$-alkylthio x—independently of the other indices x—is 0, 1 or 2, n—independently of the other indices n—is 1, 2, 3 or 4, m—independently of the other indices m—is 1 or 2, W is O or S, preferably O, X and Y independently of one another are hydrogen, halogen, $C_1$-$C_2$-alkyl, $C_1$-$C_2$-alkoxy or $C_1$-$C_2$-alkylthio, the three latter radicals being unsubstituted or substituted by one or more radicals from the group consisting of halogen, $C_1$-$C_2$-alkoxy and $C_1$-$C_2$-alkylthio, or are mono- or di-($C_1$-$C_2$-alkyl)amino, $C_3$-$C_4$-alkenyl, $C_3$-$C_4$-alkenyloxy or $C_3$-$C_4$-alkynyloxy, and Z is CH or N, preferably CH.

Also of particular interest are compounds of the formula (I) according to the invention and their salts in which G is a radical of the formula (G1) and $R^1$ is H or $C_1$-$C_3$-alkyl, preferably H or methyl, $R^2$ is $CO$-$OR^5$, $CS$-$SR^6$, $CO$-$SR^7$, $CS$-$OR^8$, $CO$-$R^9$, $CO$-$NR^{10}R^{11}$, $CO$-$O$-$N$=$CR^{12}R^{13}$, $C$(=$NR^{14}$)$R^{15}$ or $CS$-$NR^{16}R^{17}$, preferably $CO$-$OR^5$, $R^{3a}$ is H, $C_1$-$C_4$-alkyl, $C_1$-$C_4$-haloalkyl, $C_2$-$C_4$-alkenyl or $C_2$-$C_4$-alkynyl, $R^{4a}$ is CO- ($C_1$-$C_4$-alkyl), $CO_2$-($C_1$-$C_5$-alkyl) or $CO$-$NH_2$, $CO$-$NH$($C_1$-$C_4$-alkyl), $CO$-$N$($C_1$-$C_4$-alkyl)$_2$ or $SO_2$-$NH_2$-$SO_2$-$NH$($C_1$-$C_4$-alkyl) or $SO_2$-$N$($C_1$-$C_4$-alkyl)$_2$, preferably acetyl, propionyl, methoxycarbonyl, ethoxycarbonyl, propoxycarbonyl, isopropoxycarbonyl, mono- or dimethylaminocarbonyl, mono- or diethylaminocarbonyl, mono- or dipropylaminocarbonyl or mono- or diisopropylaminocarbonyl, $R^5$ is $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl or $C_4$-$C_7$-cycloalkylmethyl, $R^6$ is a radical as for $R^5$ $R^7$ is a radical as for $R^5$, $R^8$ is a radical as for $R^5$, $R^9$ is H, $C_1$-$C_4$-alkyl, $C_2$-$C_4$-alkenyl, $C_2$-$C_4$-alkynyl or $C_3$-$C_6$-cycloalkyl, the four latter radicals independently of one mother being unsubstituted or substituted by one or more radicals from the group consisting of halogen, $C_1$-$C_2$-alkoxy, $C_1$-$C_2$-alkylthio, $C_1$-$C_2$-halo-alkoxy, $C_1$-$C_2$-haloalkylthio and CN, $R^{10}$ and $R^{11}$ independently of one mother are H, $C_1$-$C_4$-alkyl, $C_2$-$C_4$-alkenyl or $C_2$-$C_4$-alkynyl, $R^{12}$ and $R^{13}$ independently of one another are H, $C_1$-$C_4$-alkyl, $C_2$-$C_4$-alkenyl or $C_2$-$C_4$-alkynyl or $R^{12}$ and $R^{13}$ together are an alkylene chain of 3 or 4 carbon atoms, which my also be substituted by $C_1$-$C_4$-alkyl or $C_1$-$C_4$-alkoxy, $R^{14}$ is $NH_2$, $NHR^{31}$, $NR^{31}_2$, $C_1-C_4$-alkyl, $C_1-C_4$-alkoxy, $C_2-C_4$-alkenyl or $C_2-C_4$-alkynyl, $R^{15}$ is H, $C_1-C_4$-alkyl, $C_1-C_4$-alkoxy, $C_2-C_4$-alkenyl or $C_2-C_4$-alkynyl, $R^{16}$ is a radical as for $R^{10}$, $R^{17}$ is a radical as for $R^{11}$, $R^{31}$ is $C_1-C_4$-alkyl, $C_2-C_4$-alkenyl or $C_2-C_4$-alkynyl, W is O or S, preferably O, X and Y independently of one another are halogen, $C_1-C_2$-alkyl, $C_1-C_2$-haloalkyl, $C_1-C_2$-alkoxy, $C_1-C_2$-haloalkoxy, $C_1-C_2$-alkylthio, mono- or di-($C_1-C_2$-alkyl)amino, $C_3-C_4$-alkenyl, $C_3-C_4$-alkenyloxy or $C_3-C_4$-alkynyloxy; preferably one radical is methyl, methoxy or chlorine and the other radical is methyl or methoxy, and Z is CH or N, preferably CH.

Also of particular interest are compounds of the formula (I) according to the invention and their salts in which G is a radical of the formula (G2) or (G3), and $R^1$ is H or $C_1-C_3$-alkyl, preferably H or methyl, $R^2$ is $CO-OR^5$, $CS-SR^6$, $CO-SR^7$, $CS-OR^8$, $CO-R^9$, $CO-NR^{10}R^{11}$, $CO-O-N=CR^{12}R^{13}$, $C(=NR^{14})R^{15}$ or $CS-NR^{16}R^{17}$, preferably $CO-OR^5$, $R^{3b}$ is H, $C_1-C_4$-alkyl, $C_3-C_6$-cycloalkyl, $C_1-C_4$-haloalkyl, $C_2-C_4$-alkenyl or $C_2-C_4$-alkynyl, $R^{4b}$ is CHO, CO- ($C_1-C_4$-alkyl), CO-($C_3-C_6$-cycloalkyl), $CO_2$-($C_1-C_4$-alkyl), CO- ($C_2-C_4$-alkenyl) or CO- ($C_2-C_4$-alkynyl), the 5 latter radicals being unsubstituted or substituted by one or more radicals from the group consisting of halogen, CN, $NR^{20}R^{21}$, S$(O)_x$-($C_1-C_4$-alkyl), $CO-NR^{22}R^{23}$ and $C_1-C_3$-alkoxy, or is $CO-NR^{24}R^{25}$, $SO_2R^{28}$ or $SO_2NR^{29}R^{30}$, $R^5$ is $C_1-C_4$-alkyl, $C_2-C_4$-alkenyl, $C_2-C_4$-alkynyl, $C_3-C_6$-cycloalkyl or $C_4-C_7$-cycloalkylmethyl, the five latter radicals being unsubstituted or substituted by one or more radicals from the group consisting of halogen, $C_1-C_2$-alkoxy and $C_1-C_2$-haloalkoxy, $R^6$ is a radical as for $R^5$, $R^7$ is a radical as for $R^5$, $R^8$ is a radical as for $R^5$, $R^9$ is H, $C_1-C_4$-alkyl, $C_2-C_4$-alkenyl, $C_2-C_4$-alkynyl or $C_3-C_6$-cycloalkyl, the four latter radicals independently of one another being unsubstituted or substituted by one or more radicals from the group consisting of halogen, $C_1-C_2$-alkoxy, $C_1-C_2$-alkylthio, $C_1-C_2$-haloalkoxy, $C_1-C_2$-haloalkylthio and CN, $R^{10}$ and $R^{11}$ independently of one another are H, $C_1-C_4$-alkyl, $C_2-C_4$-alkenyl or $C_2-C_4$-alkynyl, $R^{12}$ and $R^{13}$ independently of one another are H, $C_1-C_4$-alkyl, $C_2-C_4$-alkenyl, or $C_2-C_4$-alkynyl, or $R^{12}$ and $R^{13}$ together are an alkylene chain of 3 or 4 carbon atoms, which may also be substituted by $C_1-C_4$-alkyl or $C_1-C_4$-alkoxy, $R^{14}$ is $NH_2$, $NR^{31}$, $NR^{31}_2$, $C_1-C_4$-alkyl, $C_1-C_4$-alkoxy, $C_2-C_4$-alkenyl or $C_2-C_4$-alkynyl, $R^{15}$ is H, $C_1-C_4$-alkyl, $C_1-C_4$-alkoxy, $C_2-C_4$-alkenyl or $C_2-C_4$-alkynyl, $R^{16}$ is a radical as for $R^{10}$ $R^{17}$ is a radical as for $R^{11}$, $R^{20}$ independently of $R^{21}$ is H, $C_1-C_4$-alkyl, $C_2-C_4$-alkenyl, $C_2-C_4$-alkynyl, the radicals being unsubstituted or substituted by one or more radicals consisting of halogen and $C_1-C_2$-alkoxy, $R^{21}$ independently of $R^{20}$ is a radical as for $R^{20}$ or is CHO, CO-($C_1-C_4$-alkyl) or $CO_2$-($C_1-C_4$-alkyl) or $NR^{20}R^{21}$ together is a heterocyclic ring which, in addition to the ring nitrogen atom, may also contain a ring heteroatom from the group consisting of N, O and S, and may be substituted further by radicals from the group consisting of $C_1-C_4$-alkyl, $C_1-C_4$-alkoxy and halogen, and may, where there is a ring heteroatom S, be oxidized at the S atom, e.g. a group of the formulae K1 to K5

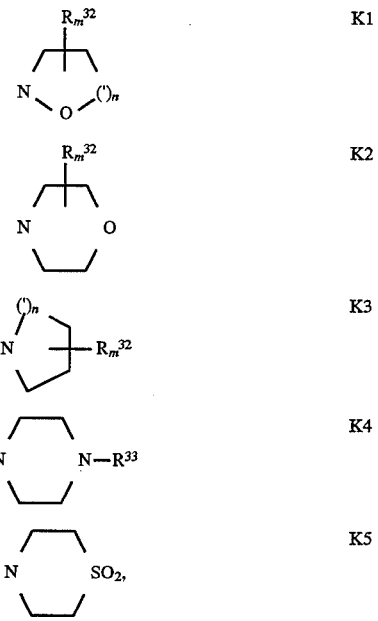

$R^{22}$ and $R^{23}$ independently of one another are H, $C_1-C_3$-alkyl, $C_2-C_4$-alkenyl or $C_2-C_4$-alkynyl or $NR^{22}R^{23}$ is a heterocyclic ring analogous to $NR^{20}R^{21}$, $R^{24}$ independently of $R^{25}$ is H, $C_1-C_4$-alkyl, $C_2-C_4$-alkenyl or $C_2-C_4$-alkynyl, the three latter radicals being unsubstituted or substituted by one or more radicals from the group consisting of halogen, $C_1-C_3$-alkoxy, $C_1-C_3$-alkylthio and CN, $R^{25}$ independently of $R^{24}$ is H, $C_1-C_4$-alkyl, $C_2-C_4$-alkenyl or $C_2-C_4$-alkynyl, the three latter radicals being unsubstituted or substituted by one or more radicals from the group consisting of halogen, $C_1-C_3$-alkoxyl, $C_1-C_3$-alkylthio and CN, or is $C_1-C_3$-alkoxy or OH, or $NR^{24}R^{25}$ is a heterocyclic ring analogous to $NR^{20}R^{21}$, $R^{28}$ is $C_1-C_4$-alkyl, $C_2-C_4$-alkenyl or $C_2-C_4$-alkynyl, the three latter radicals being unsubstituted or substituted by one or more radicals from the group consisting of halogen and $C_1-C_2$-alkoxyl, $R^{29}$ independently of $R^{30}$ is a radical as for $R^{24}$, $R^{30}$ independently of $R^{29}$ is a radical as for $R^{25}$, or $NR^{29}R^{30}$ is a heterocyclic ring analogous to $NR^{20}R^{21}$, $R^{31}$ is $C_1-C_4$-alkyl, $C_2-C_4$-alkenyl or $C_2-C_4$-alkynyl, $R^{32}$ is H, $C_1-C_3$-alkyl, $C_1-C_3$-haloalkyl, $C_1-C_3$-alkoxyalkyl, halogen or CN, $R^{33}$ is H, $C_1-C_3$-alkyl, $C_2-C_4$-alkenyl or $C_2-C_4$-alkynyl, the three latter radicals being unsubstituted or substituted by one radical from the group consisting of halogen, $C_1-C_2$-alkoxy and $C_1-C_2$-alkylthio, x—independently of the other indices x—is 0, 1 or 2, n—independently of the other indices n—is 1, 2 or 3, m—independently of the other indices m—is 1 or 2, W is O or S, preferably O, X and Y independently of one another are halogen, $C_1-C_2$-alkyl, $C_1-C_2$-haloalkyl, $C_1-C_2$-alkoxy, $C_1-C_2$-haloalkoxyl, $C_1-C_2$-alkylthio, mono- or di- ($C_1-C_2$-alkyl)amino, $C_3-C_4$-alkenyl, $C_3-C_4$-alkenyloxy or $C_3-C_4$-alkynyloxy; preferably one radical is methyl, methoxy or chlorine and the other radical is methyl or methoxy, and Z is CH or N, preferably CH.

The present invention also relates to processes for the preparation of the compounds of the formula (I) according to the invention or their salts, which comprise a) reacting a compound of the formula (II)

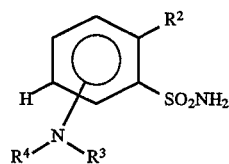

with a heterocyclic carbamate of the formula (III)

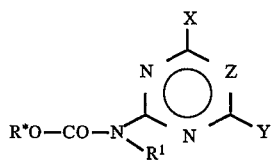

in which R* is unsubstituted or substituted phenyl or $C_1$–$C_4$-alkyl, or b) reacting a sulfonyl isocyanate of the formula (IV)

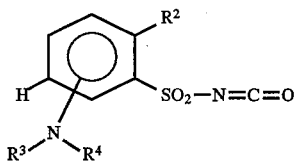

with an amino heterocycle of the formula (V)

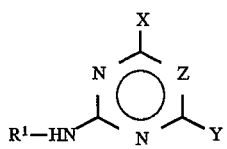

or c) reacting a sulfonyl chloride of the formula (VI)

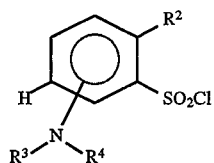

with an amino heterocycle of the abovementioned formula (V) in the presence of an isocyanate salt, for example a sodium or potassium salt, or d) reacting a sulfonamide of the abovementioned formula (II) with a (thio)isocyanate of the formula (XIX)

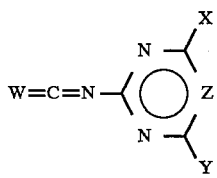

in the presence of a base, for example potassium carbonate or triethylamine, the definitions of $R^1$, $R^2$, W, X, Y and Z in the above formulae (II) to (VI) and (XIX) being as for formula (I) and, in the case of compounds of the formula (I) where G =(G1), $R^3$ and $R^4$ having the definition and position as for $R^{3a}$ and $R^{4a}$ respectively in formula (G1), and, in the case of compounds of the formula (I) where G=(G2) or (G3), $R^3$ and $R^4$ having the definition and position as for $R^{3b}$ and $R^{4b}$ respectively in formula (G2) or (G3) respectively.

The sulfonamides (II), the sulfonyl isocyanates (IV) and the sulfonyl chlorides (VI) are new compounds. The invention likewise relates to them and to their preparation.

The reaction of the compounds of the formuale (II) and (III) is preferably catalyzed by base and carried out in inert solvents such as, for example, dichloromethane, acetonitrile, dioxane or THF at temperatures from −10° C. to the boiling point of the respective solvent. Examples of bases used in this context are organic amine bases such as 1,8-diazabicyclo[5.4.0]undec-7-ene (DBU), especially when R*=(substituted) phenyl (cf. EP-A-44 807), or trimethyl- or triethylaluminum, the latter in particular when R*=alkyl (cf. EP-A-166 516).

A variety of alternatives is available for the synthesis of the compounds of the formula (II):

Starting from a compound of the formula (VII), for example 2-methyl-4-nitrobenzenesulfonic acid, the oxidation of the methyl group leads, with appropriate oxidizing agents such as potassiumpermanganate, to the corresponding carboxylic acids [in analogy to Org. Syn. Coll. Vol. 3, 740 (1955)], which are subsequently converted by acid-catalyzed esterification [cf. in this respect: Tetrahedron, 36, 2409 (1980)] using the corresponding alcohols $R^5$-OH to the esters of the formula (VIII) (Equation 1).

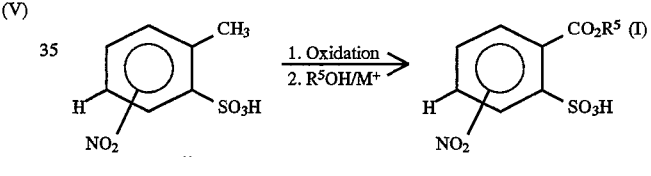

The sulfonic acids (VIII) can be transformed by known, standard methods into the N-tert-butylsulfonamides (IX): for this purpose the potassium salts, for example, of the sulfonic acids (VIII) are converted into the corresponding sulfonyl chlorides using phosphorus oxychloride or thionyl chloride, by heating at reflux in inert solvents, for example acetonitrile and/or sulfolane or without a solvent (cf. Houben-Weyl-Klamann, "Methoden der organischen Chemie" [Methods in Organic Chemistry], 4th. edition, Vol. E XI/2, pp. 1067–1073, Thieme Verlag Stuttgart, 1985). These sulfonyl chlorides are then reacted with tert-butylamine to give the sulfonamides of the formula (IX) (Equation 2). These reactions are generally carried out at temperatures of between −78° C. and +80° C., preferably at between 0° C. and 30° C., in solvents such as dichloromethane, trichloromethane, THF, dioxane, methanol or ethanol.

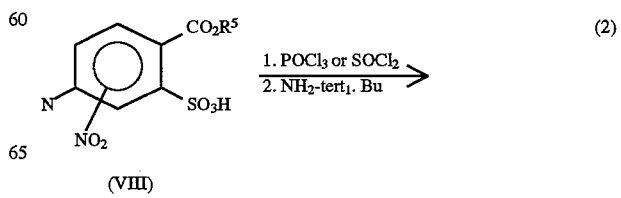

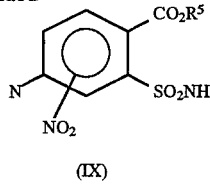

(IX)

The nitro group in the compound of the formula (IX) then reduced to the amino group (Equation 3).

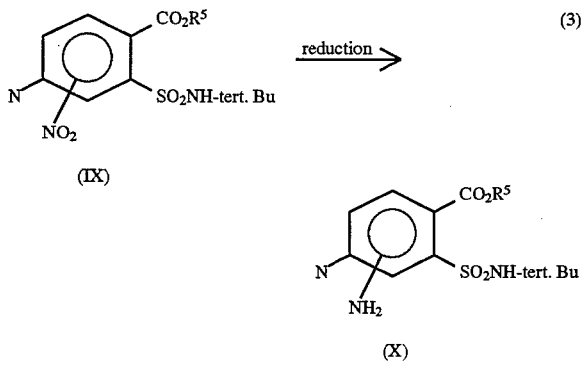

The reduction can be carried out, for example, using hydrogen in the presence of a catalyst such as Pd or using iron in an acetic acid medium [cf. in this respect: H. Berrie, G. T. Neuhold, F. S. Spring, *J. Chem. Soc.* 1952, M. Freifelder, "Catalytic Hydrogenation in Organic Synthesis: Procedures and Commentary", J. Wiley & Sons, New York (1978), chapter 5].

The resulting anilines of the formula (X) are then functionalized at the amino group: by acylation when $R^3$ is H, and by monoalkylation plus acylation when $R^3$ is not H (Equation 4).

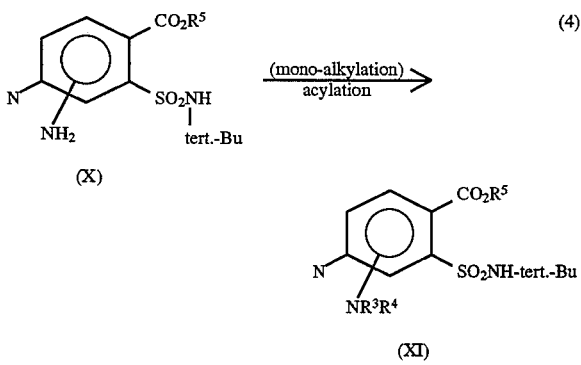

The monoalkylation of the $NH_2$ group of the compounds (X) can be carried out readily by a method of S. Krishnamurthy [Tetrahedron Lett. 23, 3315 (1982)]. The reaction with appropriate electrophiles, for example acyl chlorides, acid anhydrides, isocyanates, thioisocyanate, sulfonyl chlorides or amidosulfonylchlorides to give the N-acylated compounds (XI) can be carried out in analogy to processes known from the literature [cf. in this respect: A. L. J. Beckniter in J. Zabicky "The Chemistry of Amides", pp. 73–185, Interscience, New York, 1970; E. J. Corey et al., Tetrahedron Lett. 1978, 1051; H. J. Saunders, R. J. Slocombe, Cham. Rev. 43, 203 (1948); S. Ozaki, Chem. Rev. 72, 457, 469 (1972); G. Zoelss, Arzneim.-Forsch. 33, 2 (1983); Houben-Weyl-Hagemann, "Methoden der Organischen Chemie" [Methods in Organic Chemistry], 4th edition, Vol. E4, pp. 485 ff., Thieme Verlag Stuttgart, 1983; J. Golinsky, M. Mahosza, Synthesis 1978, 823; Houben-Weyl-Meller, "Methoden der organischen Chemie" [Methods in Organic Chemistry], 4th edition, Vol. IX, pp. 338–400 and 605–622, Thieme Verlag Stuttgart 1955; Houben-Weyl-Klamann, "Methoden der organischen Chemie" [Methods in Organic Chemistry], 4th edition, Vol. E11/2, pp. 1020–22, Thieme Verlag Stuttgart, 1985].

The elimination of the tert-butyl group from the compounds of the formula (XI) to give the sulfonamides (II) is carried out, for example, using strong acids (cf. in this respect WO 89/10921) (Equation 5).

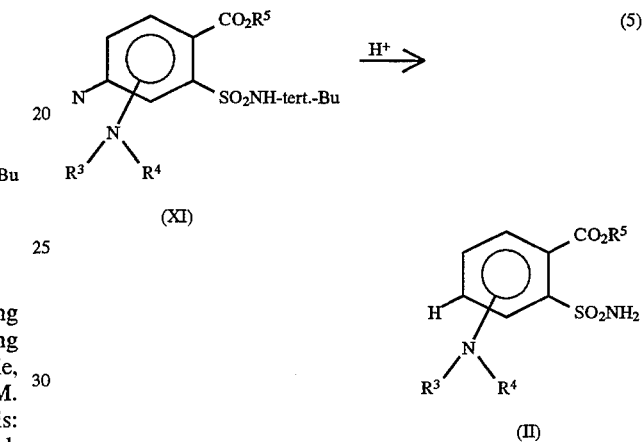

Suitable strong acids are, for example, mineral acids such as sulfuric acid or hydrochloric acid, or strong organic acids such as trifluoroacetic acid. The reactions are carried out, for example, at temperatures from $-20°$ C. to the respective reflux temperature, preferably at from $0°$ C. to $40°$ C., in an inert solvent such as dichloromethane or trichloromethane, or without solvent.

A further route to the compounds (II) is offered by the following reaction sequence (cf. Equation 6):

Starting from aminonitrotoluenes of the formula (XII), e.g. 3-amino-2-methylnitrobenzene, the substituents $R^3$ and $R^4$ are introduced by monoalkylation and acylation (in analogy to Equation 4). The resulting compounds (XIII) are subjected to an oxidation—for example using potassium permanganate—to give the carboxylic acids (by analogy with Equation 1). These benzoic acid derivatives are then esterified by known, standard methods (by analogy with Equation 1).

Equation 6:

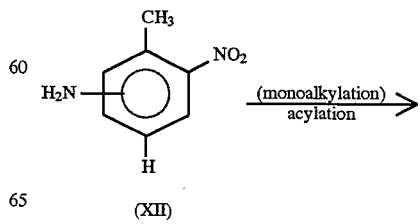

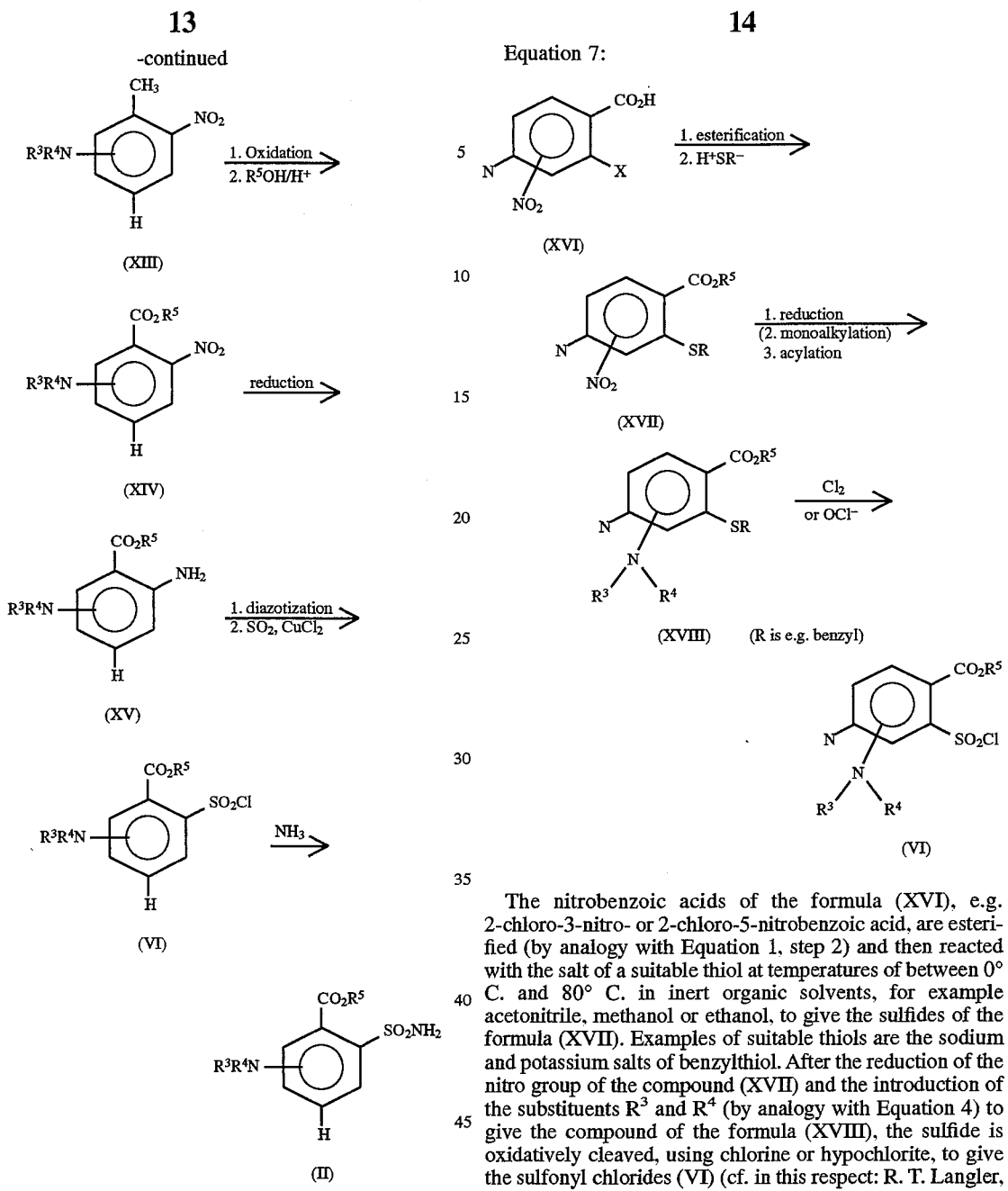

The resulting aromatic esters (XIV) can be reduced to the anilines of the formula (XV) (by analogy with Equation 3). Following the diazotization of the anilines (XV) and the subsequent reaction with sulfur dioxide, the sulfonyl chlorides (VI) are obtained (Houben-Weyl-Meller, "Meth. d. org. Chemie" [Methods in Organic Chemistry], 4th edition, Vol. IX, pp. 563 ff., Thieme Verlag Stuttgart The ammonolysis of the sulfonyl chlorides (VI) leads ultimately to the sulfonamides (II). This reaction is carried out, for example, at temperatures of between 0° C. and 40° C. in the presence of organic solvents such as tetrahydrofuran, dioxane, dichloromethane, trichloromethane, methanol, ethanol, etc.

An alternative route to the sulfonyl chlorides (VI) is made possible by the following reaction sequence (Equation 7):

The nitrobenzoic acids of the formula (XVI), e.g. 2-chloro-3-nitro- or 2-chloro-5-nitrobenzoic acid, are esterified (by analogy with Equation 1, step 2) and then reacted with the salt of a suitable thiol at temperatures of between 0° C. and 80° C. in inert organic solvents, for example acetonitrile, methanol or ethanol, to give the sulfides of the formula (XVII). Examples of suitable thiols are the sodium and potassium salts of benzylthiol. After the reduction of the nitro group of the compound (XVII) and the introduction of the substituents $R^3$ and $R^4$ (by analogy with Equation 4) to give the compound of the formula (XVIII), the sulfide is oxidatively cleaved, using chlorine or hypochlorite, to give the sulfonyl chlorides (VI) (cf. in this respect: R. T. Langler, Can. J. Chem. 54, 498 (1976); Houben-Weyl-Mueller, "Methoden der Organischen Chemie" [Methods in Organic Chemistry], 4th edition, Vol. 9, pp. 580–583, Thieme Verlag Stuttgart, 1955); these reactions are carried out at between −10° C. and 60° C., preferably between 0° C. and 15° C., in a two-phase system. Suitable examples for the aqueous phase are water, phosphate buffer solutions (pH=7) or hydrochloric acid, and for the organic phase, dichloromethane or trichloromethane.

The carbamates of the formula (III) required for the reaction of the compounds (II) in accordance with variant a) are known from the literature or can be prepared in analogy to known processes (cf. EP-A-70 804 or U.S. Pat. No. 4,480,101).

The phenylsulfonyl isocyanates of the formula (IV) can be prepared, for example, in analogy to the processes of EP-A-184 385 from compounds of the formula (II), for example using phosgene.

The reaction of the compounds (IV) with the amino heterocycles of the formula (V) is preferably carried out in inert aprotic solvents such as dioxane, acetonitrile or tetrahydrofuran at temperatures of between 0° C. and the boiling temperature of the solvent.

The reaction of the sulfonyl chlorides (VI) with the amino heterocycles of the formula (V) and isocyanate salts such as sodium isocyanate and potassium isocyanate is carried out, for example, in aprotic solvents such as acetonitrile in the presence of from 0.5 to 2 equivalents of base at temperatures of between −10° C. and 60° C., preferably at from 15° C. to 40° C. Examples of suitable bases are pyridine, picoline or lutidine, or a mixture thereof (cf. U.S. Pat. No. 5,157,119).

The (thio)isocyanates of the formula (XIX) can be obtained by processes known from the literature (EP-A-232 067, EP-A-166 516). The reaction of the (thio) isocyanates (XIX) with compounds (II) is carried out at from −10° C. to 100° C., preferably from 20° to 100° C. in an inert aprotic solvent such as acetone or acetonitrile in the presence of a suitable base, for example $N(C_2H_5)_3$ or $K2CO_3$.

The salts of the compounds of the formula (I) are preferably prepared in inert solvents, for example water, methanol, acetone, dichloromethane, tetrahydrofuran, toluene or heptane, at temperatures of from 0° to 100° C. Examples of suitable bases for the preparation of the salts according to the invention are alkali metal carbonates such as potassium carbonate, alkali metal and alkaline earth metal hydroxides such as NaOH, KOH and $Ca(OH)_2$, ammonia or an appropriate amine base such as triethylamine or ethanolamine. Examples of acids suitable for salt formation are HCl, HBr, $H_2SO_4$ or $HNO_3$.

The solvents defined as "inert" in the preceding process variants are meant to denote in each case solvents which are inert under the respective reaction conditions, but which are not necessarily inert under any reaction conditions.

The compounds of the formula (I) according to the invention or their salts have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be combated by the compounds according to the invention, without the enumeration being a restriction to certain species.

Examples of weed species on which the active substances act efficiently are, from amongst the monocotyledons, Avena, Lolium, Alopecurus, Phalaris, Echinochloa, Digitaria, Setaria and also Cyperus species from the annual sector and, from amongst the perennial species, Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemesia in the case of the perennial weeds.

The active substances according to the invention likewise effect outstanding control of weeds which occur under the specific conditions of rice-growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage, but then their growth stops, and eventually, after three to four weeks have elapsed, they die completely.

If the active substances are applied post-emergence on the green parts of the plants, growth likewise stops drastically a very short time after the treatment and the weed plants remain at the growth stage of the point in time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

In addition, the substances according to the invention exhibit outstanding growth-regulatory properties in crop plants. They intervene to regulate the phytoendogenous metabolism and can therefore be used to have a specific influence on the substances contained in plants and in order to facilitate harvesting, for example by initiating desiccation and compacted growth. Furthermore, they are also suitable for the general control and inhibition of unwanted vegetative growth, without killing the plants in the process. Inhibition of vegetative growth is very important for numerous monocotyledon and dicotyledon crops, since it allows lodging to be reduced or prevented completely.

The compounds according to the invention can be employed in the form of wettable powders, emulsifiable concentrates, sprayable solutions, dusting compositions or granules, in the customary formulations. The invention therefore relates also to herbicidal and plant growth-regulatory compositions which comprise compounds of the formula (I) or their salts.

The compounds of the formula 1 or their salts can be formulated in a variety of ways, as predetermined by the biological and/or chemicophysical parameters. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water base, oil-miscible solutions, capsule suspensions (CS), dusting agents (DP), seed-dressing agents, granules for scatter and soil application, granules (GR) in the form of microgranules, spray granules, coated granules and adsorption granules, water-dispersible granules (WG), water-soluble granules (SG) ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th ed., 1986; Wade van Valkenburg, "Pesticide Formulations", Marcel Dekker N.Y., 1973; K. Martens, "Spray Drying" Handbook, 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. V. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl achenaktive Äthylenoxidaddukte,, [Surface-active Ethylene Oxide Adducts]", Wiss. Verlagsgesell., Stuttgart 1976; Winnacker-Küchler, "Chemische Technologie" [Chemical Technology], Volume 7, C. Hauser Verlag Munich, 4th ed. 1986.

Combinations with other pesticidally active substances, for example insecticides, acaricides, other herbicides, fungicides, safeners, fertilizers and/or growth regulators may also be prepared on the basis of these formulations, for example in the form of a readymix or as a tank mix.

Wettable powders are preparations which are uniformly dispersible in water and which, besides the active substance and a diluent or inert substance, also contain ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate, or alternatively sodium oleoyl-methyltaurinate. Wettable powders are prepared by fine grinding of the herhicidal active substances in, for example, conventional apparatus such as hammer mills, blowing mills and air-jet mills and simultaneous or subsequent mixing thereof with the formulation auxiliaries.

Emulsifiable concentrates are prepared by dissolving the active substance in an organic solvent, for example butanol, cyclohexanone, dimethylformamide, xylene and also higher-boiling aromatic compounds or hydrocarbons, or mixtures of the organic solvents, with the addition of one or more ionic and/or nonionic surfactants (emulsifiers). Examples of emulsifiers which can be used are: calcium salts of an alkylarylsulfonic acid, such as Ca dodecylbenzenesulfonate, or nonionicemulsifiers, such as fatty acid polyglycol esters, alkylaryl polyglycol ethers, fatty alcohol polyglycol ethers, propylene oxide/ethylene oxide condensation products, alkyl polyethers, sorbitan esters, such as sorbitan fatty acid esters, or polyoxyethylene sorbitan esters, such as polyoxyethylene sorbitan fatty acid esters.

Dusting agents are obtained by grinding the active substance with finely divided solid substances, for example talc or natural clays, such as kaolin, bentonits and pyrophyllite, or diatomaceous earth.

Suspension concentrates may be based on water or on oil. They can be produced, for example, by wet-grinding using commercially available bead mills and, if appropriate, adding surfactants, for example as already listed above for the other formulation types.

Emulsions, for example oil-in-water emulsions (EW), can be prepared, for example, by means of stirrers, colloid mills and/or static mixers using aqueous organic solvents and, if desired, surfactants, for example as already listed above for the other formulation types.

Granules can be produced either by spraying the active substance onto adsorptive, granulated inert material or by applying active substance concentrates onto the surface of carriers, such as sand, kaolinires or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Water-dispersible granules are prepared as a rule by the conventional methods such as spray-drying, fluidized-bed granulation, plate granulation, mixing with high-speed mixers and extrusion without solid inert material.

The agrochemical formulations generally contain from 0.1 to 99% by weight, in particular from 0.1 to 95% by weight, of active substance of the formula (I) or salts thereof.

The concentration of active substance in wettable powders is, for example, about 10 to 90% by weight; the remainder to 100% by weight is composed of conventional formulation components. In the case of emulsifiable concentrates, the concentration of active substance can be about 1 to 90%, preferably 5 to 80% by weight. Formulations in the form of dusts contain 1 to 30%, usually and preferably 5 to 20% by weight of active substance, sprayable solutions about 0.05 to 80%, preferably 2 to 50% by weight of active substance. In the case of water-dispersible granules, the active substance content depends partly on whether the active compound is liquid or solid and on which granulation auxiliaries, fillers, etc. are used. In the case of water-dispersible granules, the active substance content is, for example, between 1 and 95% by weight, preferably between 10 and 80% by weight.

In addition, the active substance formulations mentioned contain, if appropriate, the adhesives, wetting agents, dispersing agents, emulsifiers, penetrants, preservatives, antifreeze agents and solvents, fillers, carriers and colorants, antifoams, evaporation inhibitors, pH modifiers and viscosity modifiers, which are conventional in each case.

Examples of combination partners for the active substances according to the invention which can be employed in mix formulations or in a tank mix are known active substances as described, for example, in Weed Research 26, 441–445 (1986) or "The Pesticide Manual", 9th edition, The British Crop Protection Council, 1990/91, Bracknell, England, and the literature cited therein. Examples of herbicides which are known from the literature and can be mentioned as possibilities for combination with the compounds of the formula (I) are the following active substances (note: the compounds are either given their "common name" according to the International Organization for Standardization (ISO) or their chemical name, together, if appropriate, with a conventional code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenyl-acetamide; CDEC, i.e. 2-chloroallyl diethyldithiocarbamate; CGA 184927, i.e. 2-[4-[(5-chloro-3-fluoro-2-pyridyl)oxy]phenoxy]propanoic acid and its 2-propynyl ester; chlomethoxyfen; chloramben; chlorazifop-butyl, pirifenop-butyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmedipham; desmetryn; di-allate; dicamba; dichlobenil; dichlorprop; diclofop-methyl;

diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]-ethanesulfonamide; F6285, i.e. 1-[5-(N-methylsulfonyl)-amino-2,4-dichlorophenyl]-3-methyl-4-difluoromethyl-1,2,4-triazol-5-one; fenoprop; fenoxan, s. clomazon; fenoxaprop-ethyl; fenuron; flamprop-methyl; flazasulfuron; fluazifop and its ester derivatives; fluchloralin; flumetsulam; N-[2,6-difluorophenyl]-5-methyl-(1, 2,4)-triazolo[1,5a]pyrimidine-2-sulfonamide; flumeturon; flumipropyn; fluorodifen; fluoroglycofen-ethyl; fluridone; flurochloridone; fluroxypyr; flurtamone; fomesafen; losamine; furyloxyfen; glufosinate; glyphosate; halosaten; haloxyfop and its ester derivatives; hexazinone; Hw 52, i.e. N-(2,3-dichlorophenyl)-4-(ethoxymethoxy) benzamide; imazamethabenz-methyl; imazapyr; imazaquin; imazethamethapyr; imazethapyr; imazosulfuron; ioxynil; isocarbamide; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N- (3-chloro-2-propenyl) -5-methyl-N-phenyl-3-pyridazinamine; MT 5950, i.e. N-[3-chloro-4-(1-methylethyl) -phenyl]-2 -methylpentanamide; naproanilide; napropamide; naptalam; NC 3 10, i. e. 4 - (2,4 -dichloro-benzoyl)-1-methy1-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometram; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofopethyl; quizalofop-p-tefuryl; renriduron; dymron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e.2-[[7-[2-chloro-4-(trifluoromethyl)phenoxy]-2-naphthyl]oxy] propenoic acid and its methyl ester; sulfometuron-methyl; sulfazuron; flazasulfuron; TCA; tebutam; tebuthiuron; terbaeil; terbucarb; terbuchlor; terbumeton; terbuthylazine; terbutryn; TFH 450, i.e. N,N-diethyl-3-[(2-ethyl-6-methylphenyl) sulfonyl]-1H-1,2,4-triazole-1-carboxamide; thiazafluron; thifensulfuronmethyl; thiobencarb; tiocarbazil; tralkoxydim; triallate; triasulfuron; triazofenamide; tribenuron-methyl; triclopyr; tridiphane; trietazine; trifluralin; trimeturon; vernolate; and WL 110547, i.e. 5-phenoxy-1-[3-(trifluoromethyl)-phenyl]-1H-tetrazole.

For use, the formulations, present in commercially available form, are diluted, if appropriate, in a customary manner, for example using water in the case of wettable powders, emulsifiable concentrates, dispersions and water-dispersible granules and are subsequently applied to the plants, parts of plants, or the industrially or agriculturally utilized terrain on which the plants are standing or in which they are growing or are present as seed. Preparations in the form of dusts or granulated preparations for soil incorporation or scattering and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.001 and 10.0 kg/ha or more of active substance; preferably, however, it is between 0.005 and 5 kg/ha.

A. Chemical Examples a) Methyl 2-chloro-3-nitrobenzoate 25.50 g (0,127 mol) of 2-chloro-3-nitrobenzoic acid are dissolved in 50 ml of MeOH, and 3 ml of concentrated sulfuric acid are added. The reaction mixture is heated at boiling for 4 h. Following the addition of 10 ml of trimethyl orthoacetate the mixture is heated at boiling for a further 2 h. After cooling to 0° C. and filtering off the solid by suction, 26.4 g (96 %) of colorless methyl 2-chloro-3-nitrobenzoate are obtained, m.p. 68-70° C.

b) Methyl 2-benzylmercapto-3-nitrobenzoate

A solution of 26.0 g (0.23 mol) of potassium tertbutylate in 400 ml of MeOH is added dropwise to a mixture of 50.0 g (0.23 mol) of methyl 2-chloro-3-nitrobenzoate and 28.81 g (0.23 mol) of benzenethiol in 200 ml of methanol. After the reaction mixture has been stirred for 6 h at room temperature and left to stand for a further 15 h it is concentrated. The residue is taken up in ethyl acetate and washed in succession with saturated $NaHCO_3$ solution, water and saturated NaCl solution. After drying over $MgSO_4$ the solution is concentrated under reduced pressure. The oily-yellowish residue (68.5 g, 97% of theory) is employed for the subsequent reactions without further purification (cf. Example c).

c) Methyl 3-amino-2-benzylmercaptobenzoate 69.8 g of iron powder are added in portions to a mixture of 68.0 g (0.22 mol) of methyl 2-benzylmercapto-3-nitrobenzoate, 215 ml of glacial acetic acid and 480 ml of water. The reaction solution is then stirred at 50°–60° C. for 3 h. The solid is separated off by filtration and then the mother liquor is washed with water and salt and subsequently dried over $MgSO_4$. After concentration of the solution under reduced pressure, 47.1 g of a yellow oil (77%) are obtained; $^1H$ NMR ($CDCl_3$, 80 MHz): δ=3.8 (s, 3H, $OCH_3$), 3.9 (s, 2H, $SCH_2Ph$), 5.9 (s, 2H, $NH_2$), 6.6–7.3 (m, 8H, $H_{arom.}$).

d) Methyl 2-benzylmercapto-3-formylaminobenzoate 27.0 g (0.586 mol) of formic acid are added dropwise to 48.6 g (0.476 mol) of acetic anhydride at 0° C. After the mixture has been stirred at 50°–60° C. for 2 h it is cooled to 0° C. and a solution of 50.0 g (0.183 mol) of methyl 3-amino-2-benzylmercaptobenzoate in 150 ml of THF is added. The reaction solution is then stirred at room temperature for 4 h. The mixture is concentrated under reduced pressure (60° C., 0.1 torr). The resulting oily residue (61.77 g) is employed in subsequent reactions without further purification (cf. Example e)).

e) Methyl 2-benzylmercapto-3-methylaminobenzoate 20 ml of borane/dimethyl sulfide complex (BMS) are added dropwise to a solution of 61.5 g of methyl 2-benzylmercapto-3-formylaminobenzoate (cf. Example d)) in 100 ml of CHCl$_3$ at 0° C. The mixture is subsequently heated at 60° C. for 2 h, a further 20 ml of BMS are added, and the mixture is stirred at this temperature for a further 2.5 h. Then 30 ml of MeOH are added dropwise at 0° C. The mixture is transferred to a separating funnel, washed with water and brine and then dried over MgSO$_4$. Volatile components are removed by distillation to give 54.60 g of methyl 2-benzylmercapto-3-methylaminobenzoate in the form of a yellowish oil. $^1$H NMR (CDCl$_3$, 80 MHz): δ:2.6 (d, 3H, NH-CH$_3$), 3.8 (s, 3H, OCH$_3$), 3.9 (s, 2H, SCH$_2$Ph), 5.2 (s, broad, 1H, NH-Me), 6.5 (d, 1H, H$_{arom.}$), 6.8 (d, 1H, H$_{arom.}$), 7.0–7.4 (m, 6H, H$_{arom.}$).

f) Methyl 2-benzylmercapto-3-(N-methoxycarbonylmethylamino)benzoate 4.6 ml of methyl chloroformate are added dropwise to a suspension of 15.0 g (0.052 mol) of methyl 2-benzylmercapto-3-methylaminobenzoate and 5.88 g (0.07 mol) of sodium hydrogen carbonate in 100 ml of CH$_2$CN. After 5 h volatile components are removed by distillation (15 torr, 40° C.). The residue is taken up in ethyl acetate and washed in succession with 1 N hydrochloric acid and water. The organic phase is dried over MgSO$_4$ and then the solvent is removed by distillation. Methyl 2-benzylmercapto-3-(N-methoxycarbonylmethylamino)benzoate is obtained in the form of a yellowish oil )14.8 g); $^1$H NMR (CDCl$_3$, 80 MHz): δ=3.0 (s, 3H, N-CH$_3$), 3.6 (s, 3H, O-CH$_3$), 3.9 (s, 5H, OCH$_3$ and SCH$_2$Ph), 7.1–7.6 (m, 8H, H$_{arom.}$).

g) Methyl 2-chlorosulfonyl-3-(N-methoxycarbonylmethylamino) benzoate

Chlorine is passed at a temperature between 0° C. and 5° C. into a mixture of 8.10 g of methyl 2-benzylmercapto-3-(N-methoxycarbonylmethylamino)benzoate in 50 ml of CH$_2$Cl$_2$ and 150 ml of potassium dihydrogen phosphate/disodium hydrogen phosphate solution (Riedel-de-Haën AG, pH=7). After 30 min argon is passed through the reaction apparatus in order to remove excess chlorine. After phase separation the organic phase is dried over MgSO$_4$ and then concentrated under reduced pressure. Crystallization from ethyl acetate/hexane gives 4.5 g of methyl 2-chlorosulfonyl-3-(N-methoxycarbonylmethylamino)benzoate; m.p. 102°–105° C.

h) N-[(4-dimethylamino-6-trifluoroethoxytriazin-2-yl)-aminocarbonyl]-2-methoxycarbonyl-6-(N-methoxycarbonylmethylamino)benzenesulfonamide (Table 1, Example 24)

In succession, 0.71 g (0.003 mol) of 2-amino-4-dimethylamino-6-(2,2,2-trifluorofluoroethoxy)triazine and 1.0 g (0.003 mol) of methyl 2-chlorosulfonyl-3-(N-methoxycarbonylmethylamino)benzoate are added at room temperature to a suspension of 0.25 g (0.0038 mol) of NaOCN, 0.6 ml of pyridine and 12 ml of acetonitrile. The reaction mixture is stirred at room temperature for 3.5 h and then poured into ice-water. For purification the sulfonylurea which is separated out is stirred in a little methanol, separated off by filtration and dried. The sulfonylurea is obtained as a colorless solid (0.75 g). m.p.: 125°–126° C.

i) N-[(4,6-Dimethoxypyrimidin-2-yl)aminocarbonyl]-2-methoxycarbonyl-6-(N-methoxycarbonylmethylamino)-benzenesulfonamide (Table 1, Example 13)

In succession, 0.54 g of 2-amino-4,6-dimethoxypyrimidine and 1.50 g of methyl 2-chlorosulfonyl-3-(N-methoxycarbonylmethylamino) benzoate are added at room temperature to a suspension of 0.61 g of sodium cyanate, 0.8 ml of pyridine and 18 ml of acetonitrile. The reaction mixture is stirred at room temperature for 3.5 h and then poured into ice-water. For purification the sulfonylurea which is separated out is stirred in a little methanol, separated off by means of filtration and dried. The resulting N-[(4,6-dimethoxypyrimidin-2-yl)amino-carbonyl]-2-methoxycarbonyl-6-(N-methoxycarbonylmethylamino)benzenesulfonamide is obtained as a colorless solid (1.35 g) 150°–154° C.

j) N-[(4,6-Dimethoxypyrimidin-2-yl)aminocarbonyl]-2-methoxycarbonyl-4-(N-methoxycarbonylmethylamino)benzenesulfonamide (Table 2, Example 80)

0.6 ml of DBU are added dropwise at 0° C. to a mixture of 0.87 g of 2-methoxycarbonyl-4-(N-methoxycarbonylmethyl-amino)benzenesulfonamide and 0.90 g of 4,6-dimethoxy-2-phenoxycarbonylaminopyrimidine in 10 ml of acetonitrile. The reaction solution is then stirred at room temperature for 6 h. After removal of the solvent by distillation the residue is taken up in water and washed with diethyl ether. After acidification of the aqueous phase with concentrated hydrochloric acid (pH=1) the sulfonylurea which is separated out is stirred in a little methanol. The colorless solid is separated off by filtration and dried to give 1.18 g of N-[(4,6-dimethoxpyrimidin-2-yl)aminocarbonyl]-2-methoxycarbony1-4-(N-methoxycarbonyl-methylamino)benzenesulfonamide7 m.p.: 184°–186° C. (decomposition). The above process is repeated using the following starting quantities: 31.8 g of the benzene-sulfonamide employed, 58.0 9 of the pyrimidine employed, 150 ml of acetonitrile and 39.4 ml of DBU. After reaction at room temperature for 4 h and work-up as described above, 45.0 g of product with a melting point of 187°–189° C. are obtained.

k) N-[(4,6-dimethoxypyrimidin-2-yl)aminocarbonyl]-2-methoxycarbonyl-4-(N-methoxycarbonylmethylamino)-benzenesulfonamide, sodium salt (Table 4, Example 1)

0.53 g of N-[(4,6-dimethylpyrimidin-2-yl)aminocarbonyl]-2-methoxycarbony1-4-(N-methoxycarbonylmethylamino)benzenesulfonamide are stirred in 50 ml of $CH_2Cl_2$ and 30 ml of $CH_3CN$ at room temperature, and 1.1 ml of 1 N sodium hydroxide solution are added. The reaction solution is stirred for 2 h and then concentrated under reduced pressure (50° C., 0.1 torr). The colorless salt (0.59 g) is obtained as a colorless solid; m.p.: 155°–158° C.;

if 15.0 g of the substituted benzenesulfonamide, 120 ml of $CH_3CN$ as the sole solvent and 30 ml of 1 N sodium hydroxide solution are employed, then 16.2 g of product with a melting point of 166° C. (decomposition) are obtained accordingly.

The compounds described in the subsequent Tables 1 to 4 are obtained by or in analogy to the above Examples h) to k).

Abbreviations in Tables 1–4:

| Tab.Ex. | = Table, Example No. |
|---|---|
| m.p. | = melting point (solidification point) |
| Et | = ethyl |
| Me | = methyl |
| Pr | = $^n$Pr = n-Propyl |
| $^i$Pr | = isopropyl |
| $^c$Pr | = cyclopropyl |
| (d) | = (decomp.) = decomposition point, m.p. with decomposition |
| $CH_2CCH$ | = propargyl |

TABLE 1

| Tab. Ex. | $R^1$ | $R^5$ | $R^{3a}$ | $R^{4a}$ | X | Y | Z | m.p. [°C.] |
|---|---|---|---|---|---|---|---|---|
| 1.1 | H | Me | H | $CO_2Me$ | OMe | OMe | CH | |
| 1.2 | H | Me | H | $CO_2Me$ | OMe | Cl | CH | |
| 1.3 | H | Me | H | $CO_2Me$ | OMe | Me | N | |
| 1.4 | H | Me | H | $CO_2Et$ | OMe | OMe | CH | |
| 1.5 | H | Me | H | $CO_2Et$ | OMe | Cl | CH | |
| 1.6 | H | Me | H | $CO_2Et$ | OMe | Me | N | |
| 1.7 | H | Me | H | $CO_2{}^iPr$ | OMe | OMe | CH | |
| 1.8 | H | Me | H | CONHEt | OMe | OMe | CH | |
| 1.9 | H | Me | H | $CONH^nPr$ | OMe | OMe | CH | |
| 1.10 | H | Me | H | $COCH_3$ | OMe | OMe | CH | |
| 1.11 | H | Me | H | $COCH_3$ | OMe | Cl | CH | |
| 1.12 | H | Me | H | $COCH_3$ | OMe | Me | N | |
| 1.13 | H | Me | Me | $CO_2Me$ | OMe | OMe | CH | 150–4 (Decomp.) |
| 1.14 | H | Me | Me | $CO_2Me$ | OMe | Cl | CH | 145–9 (Decomp.) |
| 1.15 | H | Me | Me | $CO_2Me$ | Me | Me | CH | |
| 1.16 | H | Me | Me | $CO_2Me$ | OMe | Me | N | |
| 1.17 | Me | Me | Me | $CO_2Me$ | OMe | Me | N | |
| 1.18 | Me | Me | Me | $CO_2Me$ | OMe | OMe | CH | |
| 1.19 | H | Me | Me | CONHEt | OMe | OMe | CH | |
| 1.20 | H | Me | Me | CONHEt | OMe | Cl | CH | |
| 1.21 | H | Me | Et | $CO_2Me$ | OMe | OMe | CH | |
| 1.22 | H | Me | $CH_2CF_3$ | $CO_2Me$ | OMe | OMe | CH | |
| 1.23 | H | Me | Me | $CO_2CH_2CH_2Cl$ | OMe | OMe | CH | |
| 1.24 | H | Me | Me | $CO_2Me$ | $NMe_2$ | $OCH_2CF_3$ | N | 125–6 (Decomp.) |

TABLE 2

Structure: Benzene ring with CO₂R⁵ (ortho), SO₂NH—CO—N(R¹)—C(=N)-pyrimidine with X, Y, Z substituents; R³ᵇ(N)R⁴ᵇ on benzene.

| Tab. Ex. | R¹ | R⁵ | R³ᵇ | R⁴ᵇ | X | Y | Z | m.p. [°C.] |
|---|---|---|---|---|---|---|---|---|
| 2.1 | H | Me | H | COCH₃ | OMe | OMe | CH | 135–8 (Decomp.) |
| 2.2 | H | Me | H | COCH₃ | OMe | Cl | CH | |
| 2.3 | H | Me | H | COCH₃ | Me | Me | CH | |
| 2.4 | H | Me | H | COCH₃ | OMe | Me | N | |
| 2.5 | H | Me | H | COCH₃ | OMe | OMe | N | |
| 2.6 | H | Me | H | COCH₃ | SMe | SMe | N | |
| 2.7 | Me | Me | H | COCH₃ | OMe | OMe | CH | |
| 2.8 | Me | Me | H | COCH₃ | OMe | Me | N | |
| 2.9 | H | Me | H | COEt | OMe | OMe | CH | |
| 2.10 | H | Me | H | COEt | OMe | Cl | CH | |
| 2.11 | H | Me | H | COEt | OMe | Me | N | |
| 2.12 | H | Me | H | COⁱPr | OMe | OMe | CH | |
| 2.13 | H | Me | H | COⁱPr | OMe | Cl | CH | |
| 2.14 | H | Me | H | CHO | OMe | Cl | CH | |
| 2.15 | H | Me | H | CHO | OMe | OMe | CH | 205–6 (Decomp.) |
| 2.16 | Me | Me | H | COCH=CH₂ | OMe | OMe | CH | |
| 2.17 | H | Me | H | COC(Cl)=CCl₂ | OMe | OMe | CH | |
| 2.18 | H | Me | H | CO—ᶜPr | OMe | OMe | CH | |
| 2.19 | H | Me | H | CO—ᶜPr | OMe | Cl | CH | |
| 2.20 | Me | Me | H | CHO | OMe | OMe | CH | |
| 2.21 | H | Me | H | CO₂Me | OMe | OMe | CH | |
| 2.22 | H | Me | H | CO₂Me | OMe | Cl | CH | |
| 2.23 | H | Me | H | CO₂Me | OMe | Me | N | |
| 2.24 | H | Me | H | CO₂Me | OMe | OMe | N | |
| 2.25 | Me | Me | H | CO₂Me | OMe | Me | N | |
| 2.26 | H | Me | H | CO₂Et | OMe | OMe | CH | |
| 2.27 | H | Me | H | CO₂Et | OMe | Cl | CH | |
| 2.28 | H | Me | H | CO₂Et | OMe | Me | N | |
| 2.29 | H | Me | H | CO₂ⁿPr | OMe | Me | N | |
| 2.30 | H | Me | H | CO₂ⁿPr | OMe | OMe | CH | |
| 2.31 | H | Me | H | CO₂ⁿPr | OMe | Cl | CH | |
| 2.32 | H | Me | H | CO₂ⁱPr | OMe | Cl | CH | |
| 2.33 | H | Me | H | CO₂ⁱPr | OMe | OMe | CH | |
| 2.34 | H | Me | H | CO₂CH₂CH₂Cl | OMe | OMe | CH | |
| 2.35 | H | Me | H | CO₂CH₂CH₂Cl | OMe | Cl | CH | |
| 2.36 | H | Me | H | CONHEt | OMe | Cl | CH | |
| 2.37 | H | Me | H | CONHEt | OMe | OMe | CH | |
| 2.38 | H | Me | H | CONHⁿPr | OMe | OMe | CH | |
| 2.39 | H | Me | H | CONHⁿPr | OMe | Cl | CH | |
| 2.40 | H | Me | H | CONH-Allyl | OMe | Cl | CH | |
| 2.41 | H | Me | H | CONH-Allyl | OMe | OMe | CH | |
| 2.42 | H | Me | H | CO—NH—OMe | OMe | OMe | CH | |
| 2.43 | H | Me | H | CO—NH—OMe | OMe | Cl | CH | |
| 2.44 | H | Me | H | CO—NH—OMe | OMe | Me | N | |
| 2.45 | H | Me | H | CO—NMe—OMe | OMe | OMe | CH | |
| 2.46 | H | Me | H | CO—NMe—OMe | OMe | Cl | CH | |
| 2.47 | H | Me | H | SO₂Me | OMe | Cl | CH | |
| 2.48 | H | Me | H | SO₂Me | OMe | OMe | CH | |
| 2.49 | H | Me | H | SO₂Me | OMe | Me | N | |
| 2.50 | H | Me | H | SO₂CH₂Cl | OMe | OMe | CH | |
| 2.51 | H | Me | H | SO₂CH₂Cl | OMe | Cl | CH | |
| 2.52 | H | Me | H | SO₂CH₂Cl | OMe | Me | N | |
| 2.53 | H | Me | H | SO₂NHMe | OMe | OMe | CH | |
| 2.54 | H | Et | H | CO₂Me | OMe | OMe | CH | |
| 2.55 | H | Et | H | CO₂Me | OMe | Cl | CH | |
| 2.56 | H | Et | H | CO₂Me | OMe | Me | N | |
| 2.57 | H | Et | H | COMe | OMe | Cl | CH | |
| 2.58 | H | Et | H | COMe | OMe | OMe | CH | |
| 2.59 | H | ⁿPr | H | CO₂Me | OMe | OMe | CH | |
| 2.60 | H | ⁱPr | H | CO₂Me | OMe | OMe | CH | |
| 2.61 | H | Allyl | H | CO₂Me | OMe | OMe | CH | |
| 2.62 | H | CH₂CCH | H | CO₂Me | OMe | OMe | CH | |
| 2.63 | H | CH₂CH₂Cl | H | CO₂Me | OMe | OMe | CH | |
| 2.64 | H | Me | Me | CHO | OMe | OMe | CH | |
| 2.65 | H | Me | Me | CHO | OMe | Cl | CH | |

TABLE 2-continued

| Tab. Ex. | R¹ | R⁵ | R³ᵇ | R⁴ᵇ | X | Y | Z | m.p. [°C.] |
|---|---|---|---|---|---|---|---|---|
| 2.66 | H | Me | Me | CHO | OMe | Me | N | |
| 2.67 | H | Me | Me | COMe | OMe | Me | N | |
| 2.68 | H | Me | Me | COMe | OMe | OMe | CH | |
| 2.69 | H | Me | Me | COMe | OMe | Cl | CH | 181–3 (Decomp.) |
| 2.70 | H | Me | Me | COEt | OMe | Cl | CH | |
| 2.71 | H | Me | Me | COEt | OMe | OMe | CH | |
| 2.72 | H | Me | Me | CO$^i$Pr | OMe | OMe | CH | |
| 2.73 | H | Me | Me | COCH$_2$Cl | OMe | OMe | CH | |
| 2.74 | H | Me | Me | COCH$_2$Cl | OMe | Cl | CH | |
| 2.75 | H | Me | Me | COCH$_2$Cl | OMe | Me | N | |
| 2.76 | H | Me | Me | COCHCl$_2$ | OMe | OMe | CH | |
| 2.77 | H | Me | Me | COCF$_3$ | OMe | OMe | CH | |
| 2.78 | H | Me | Me | COCF$_3$ | OMe | Cl | CH | |
| 2.79 | H | Me | Me | CO$_2$Me | OMe | Cl | CH | |
| 2.80 | H | Me | Me | CO$_2$Me | OMe | OMe | CH | 187–9 (Decomp.) |
| 2.81 | H | Me | Me | CO$_2$Me | OMe | Me | N | 177 (Decomp.) |
| 2.82 | Me | Me | Me | CO$_2$Me | OMe | Me | N | |
| 2.83 | Me | Me | Me | CO$_2$Me | OMe | OMe | CH | |
| 2.84 | H | Me | Me | CO$_2$Me | NMe$_2$ | OCH$_2$CF$_3$ | N | |
| 2.85 | H | Me | Me | CO$_2$Et | OMe | Cl | CH | |
| 2.86 | H | Me | Me | CO$_2$Et | OMe | OMe | CH | |
| 2.87 | H | Me | Me | CO$_2$$^i$Pr | OMe | OMe | CH | |
| 2.88 | H | Me | Me | CO$_2$-Allyl | OMe | OMe | CH | |
| 2.89 | H | Me | Me | CONHPr | OMe | OMe | CH | |
| 2.90 | H | Me | Me | CONHPr | OMe | Cl | CH | |
| 2.91 | H | Me | Me | CONHEt | OMe | Cl | CH | |
| 2.92 | H | Me | Me | CONHEt | OMe | OMe | CH | 160–3 (Decomp.) |
| 2.93 | H | Me | Me | CONHOMe | OMe | OMe | CH | |
| 2.94 | H | Me | Me | CONHOMe | OMe | Cl | CH | |
| 2.95 | H | Me | Me | CONMeOMe | OMe | OMe | CH | |
| 2.96 | H | Me | Me | CONMeOMe | OMe | Cl | CH | |
| 2.97 | H | Me | Me | CONMe$_2$ | OMe | Cl | CH | |
| 2.98 | H | Me | Me | CONMe$_2$ | OMe | OMe | CH | |
| 2.99 | H | Me | Me | CO$_2$CH$_2$CH$_2$Cl | OMe | OMe | CH | |
| 2.100 | H | Me | Me | CO$_2$CH$_2$CH$_2$Cl | OMe | Cl | CH | |
| 2.101 | H | Me | Me | CO$_2$CH$_2$CH$_2$Cl | OMe | Me | N | 171–2 (Decomp.) |
| 2.102 | H | Me | Et | CO$_2$Me | OMe | OMe | CH | |
| 2.103 | H | Me | Et | CO$_2$Me | OMe | Cl | CH | |
| 2.104 | H | Me | Et | COCH$_3$ | OMe | Cl | CH | |
| 2.105 | H | Me | Et | COCH$_3$ | OMe | OMe | CH | 153–6 (Decomp.) |
| 2.106 | H | Me | Et | CHO | OMe | OMe | CH | 112–4 (Decomp.) |
| 2.107 | H | Me | Et | CHO | OMe | Cl | CH | |
| 2.108 | H | Me | Allyl | CO$_2$Me | OMe | OMe | CH | |
| 2.109 | H | Me | CH$_2$CCH | CO$_2$Me | OMe | OMe | CH | |
| 2.110 | H | Me | $^i$Pr | CO$_2$Me | OMe | OMe | CH | |
| 2.111 | H | Me | CH$_2$–$^c$Pr | CO$_2$Me | OMe | OMe | CH | |
| 2.112 | H | Me | CH$_2$–$^c$Pr | SO$_2$Me | OMe | OMe | CH | |
| 2.113 | H | Me | CH$_2$–$^c$Pr | SO$_2$Me | OMe | Cl | CH | |
| 2.114 | H | Me | CH$_2$–$^c$Pr | SO$_2$Me | OMe | Me | N | |
| 2.115 | H | Me | CH$_2$–$^c$Pr | SO$_2$CH$_2$Cl | OMe | Me | N | |
| 2.116 | H | Me | CH$_2$–$^c$Pr | SO$_2$CH$_2$Cl | OMe | Cl | CH | |
| 2.117 | H | Me | CH$_2$–$^c$Pr | SO$_2$CH$_2$Cl | OMe | OMe | CH | |
| 2.118 | H | Me | CH$_2$–$^c$Pr | SO$_2$NHMe | OMe | OMe | CH | |
| 2.119 | H | Me | H | COCF$_3$ | OMe | OMe | CH | 122–5 (Decomp.) |
| 2.120 | H | Me | $^n$Pr | COCH$_3$ | OMe | OMe | CH | 110–2 (Decomp.) |
| 2.121 | H | Me | $^n$Pr | CHO | OMe | OMe | CH | 177 (Decomp.) |

TABLE 2-continued

| Tab. Ex. | R¹ | R⁵ | R³ᵇ | R⁴ᵇ | X | Y | Z | m.p. [°C.] |
|---|---|---|---|---|---|---|---|---|
| 2.122 | H | Me | Me | CSNHMe | OMe | OMe | CH | 160–3 (Decomp.) |
| 2.123 | H | Me | Me | SO₂Me | OMe | OMe | CH | 159–61 (Decomp.) |
| 2.124 | H | Me | ⁿPr | COOMe | OMe | OMe | CH | 133–6 (Decomp.) |
| 2.119 | H | Me | Me | COOMe | OMe | OMe | N | 165 (Decomp.) |

TABLE 3

| Tab. Ex. | R¹ | R⁵ | R³ᵇ | R⁴ᵇ | X | Y | Z | m.p.(°C.) |
|---|---|---|---|---|---|---|---|---|
| 3.1 | H | Me | H | CHO | OMe | OMe | CH | |
| 3.2 | H | Me | H | CHO | OMe | Cl | CH | |
| 3.3 | H | Me | H | CHO | OMe | Me | N | |
| 3.4 | H | Me | H | COCH₃ | OMe | OMe | N | |
| 3.5 | H | Me | H | COCH₃ | OMe | OMe | CH | |
| 3.6 | H | Me | H | COCH₃ | OMe | Cl | CH | |
| 3.7 | H | Me | H | COCH₃ | OMe | Me | N | |
| 3.8 | H | Me | H | COCH₃ | SMe | SMe | N | |
| 3.9 | H | Me | H | COCH₃ | NMe₂ | OCH₂CF₃ | N | |
| 3.10 | Me | Me | H | COCH₃ | OMe | Me | N | |
| 3.11 | H | Me | H | COCH₂Cl | OMe | Me | N | |
| 3.12 | H | Me | H | COCH₂Cl | OMe | Cl | CH | |
| 3.13 | H | Me | H | COCH₂Cl | OMe | OMe | CH | |
| 3.14 | H | Me | H | COCHCl₂ | OMe | Me | N | |
| 3.15 | H | Me | H | COCHCl₂ | OMe | Cl | CH | |
| 3.16 | H | Me | H | COCHCl₂ | OMe | OMe | CH | |
| 3.17 | H | Me | H | COCF₃ | OMe | OMe | CH | |
| 3.18 | H | Me | H | CO—ⁱPr | OMe | Cl | CH | |
| 3.19 | H | Me | H | CO—ⁱPr | OMe | OMe | CH | |
| 3.20 | H | Me | H | CO—ᶜPr | OMe | Cl | CH | |
| 3.21 | H | Me | H | CO—ᶜPR | OMe | OMe | CH | |
| 3.22 | H | Me | H | CO₂Me | OMe | OMe | CH | |
| 3.23 | H | Me | H | CO₂Me | OMe | Me | N | |
| 3.24 | H | Me | H | CO₂Me | NMe₂ | OCH₂CF₃ | N | |
| 3.25 | H | Me | H | CO₂Et | OMe | Me | N | |
| 3.26 | H | Me | H | CO₂Et | OMe | OCH₂CF₃ | N | |
| 3.27 | H | Me | H | CO₂Et | OMe | Cl | CH | |
| 3.28 | H | Me | H | CO₂Et | OMe | OMe | CH | |
| 3.29 | H | Me | H | CO₂CH₂CH₂Cl | OMe | Cl | N | |
| 3.30 | H | Me | H | CO₂CH₂CH₂Cl | OMe | OMe | CH | |
| 3.31 | H | Me | H | COHNEt | OMe | OMe | CH | |
| 3.32 | H | Me | H | CONHEt | OMe | Cl | CH | |
| 3.33 | H | Me | H | CONMe₂ | OMe | OMe | CH | |
| 3.34 | H | Me | H | CON(pyrrolidinyl) | OMe | OMe | CH | |
| 3.35 | H | Me | H | CO—N(morpholinyl) | OMe | OMe | CH | |

TABLE 3-continued

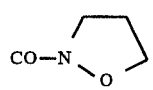

| Tab. Ex. | R¹ | R⁵ | R³ᵇ | R⁴ᵇ | X | Y | Z | m.p.(°C.) |
|---|---|---|---|---|---|---|---|---|
| 3.36 | H | Me | H | 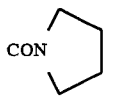 | OMe | OMe | CH | |
| 3.37 | H | Me | H | CON(Me)OMe | OMe | OMe | CH | |
| 3.38 | H | Me | H | CO—NH—OMe | OMe | OMe | CH | |
| 3.39 | Me | Me | H | CO₂Me | OMe | Cl | CH | |
| 3.40 | Me | Me | H | CO₂Me | OMe | OMe | CH | |
| 3.41 | Me | Me | H | CO—CH₃ | OMe | OMe | CH | |
| 3.42 | Me | Me | Me | CO—CH₃ | OMe | Cl | CH | |
| 3.43 | H | Me | Me | CHO | OMe | OMe | CH | |
| 3.44 | H | Me | Me | CHO | OMe | Cl | CH | |
| 3.45 | H | Me | Me | CHO | OMe | Me | N | |
| 3.46 | H | Me | Me | COCH₃ | OMe | OMe | CH | |
| 3.47 | H | Me | Me | CO—CH₃ | OMe | Me | N | |
| 3.48 | H | Me | Me | CO—CH₃ | OMe | Cl | CH | |
| 3.49 | H | Me | Me | COCF₃ | OMe | Cl | CH | |
| 3.50 | H | Me | Me | COCF₃ | OMe | OMe | CH | |
| 3.51 | H | Me | Me | COCHCl₂ | OMe | OMe | CH | |
| 3.52 | H | Me | Me | CO—ᶜPr | OMe | OMe | CH | |
| 3.53 | H | Me | Me | COCH₂Cl | OMe | OMe | CH | |
| 3.54 | H | Me | Me | CO₂Me | OMe | OMe | CH | |
| 3.55 | H | Me | Me | CO₂Me | OMe | Cl | CH | |
| 3.56 | H | Me | Me | CO₂Me | OMe | Me | N | |
| 3.57 | H | Me | Me | CO₂Me | Me | Me | N | |
| 3.58 | H | Me | Me | CO₂Et | OMe | OMe | CH | |
| 3.59 | H | Me | Me | CO₂Et | OMe | Cl | CH | |
| 3.60 | H | Me | Me | CO₂ⁱPr | OMe | OMe | CH | |
| 3.61 | H | Me | Me | CO₂CH₂CH₂Cl | OMe | Cl | CH | |
| 3.62 | H | Me | Me | CO₂CH₂CH₂Cl | OMe | OMe | CH | |
| 3.63 | H | Me | Me | CONMe₂ | OMe | Cl | CH | |
| 3.64 | H | Me | Me | CONHEt | OMe | Cl | CH | |
| 3.65 | H | Me | Me | CONHEt | OMe | OMe | CH | |
| 3.66 | H | Me | Me | CONHOMe | OMe | OMe | CH | |
| 3.67 | H | Me | Me | CONHOMe | OMe | Cl | CH | |
| 3.68 | H | Me | Me | CONMeOMe | OMe | OMe | CH | |
| 3.69 | Me | Me | Me | COCH₃ | OMe | OMe | CH | |
| 3.70 | Me | Me | Me | COCH₃ | OMe | Cl | CH | |
| 3.71 | Me | Me | Me | COCH₃ | OMe | Me | N | |
| 3.72 | Me | Me | Me | CHO | OMe | OMe | CH | |
| 3.73 | Me | Me | Me | CHO | OMe | Me | N | |
| 3.74 | Me | Me | Me | CO₂Me | OMe | Me | N | |
| 3.75 | Me | Me | Me | CO₂Me | OMe | OMe | CH | |
| 3.76 | H | Me | Et | CHO | OMe | OMe | CH | |
| 3.77 | H | Me | Et | CHO | OMe | Cl | CH | |
| 3.78 | H | Me | Et | COCH₃ | OMe | Cl | CH | |
| 3.79 | H | Me | Et | COCH₃ | OMe | OMe | CH | |
| 3.80 | H | Me | Et | CO₂Me | OMe | OMe | CH | |
| 3.81 | H | Me | Et | CO₂Me | OMe | Cl | CH | |
| 3.82 | H | Me | Et | CONMe₂ | OMe | OMe | CH | |
| 3.83 | H | Me | Et | CONMe₂ | OMe | Cl | CH | |
| 3.84 | H | Me | Et | CO—NMe—OMe | OMe | OMe | CH | |
| 3.85 | H | Me | Et | CO—NH—OMe | OMe | OMe | CH | |
| 3.86 | H | Me | ⁿPr | CHO | OMe | OMe | CH | |
| 3.87 | H | Me | ⁿPr | COCH₃ | OMe | OMe | CH | |
| 3.88 | H | Me | ⁿPr | CO₂Me | OMe | OMe | CH | |
| 3.89 | H | Me | Me | 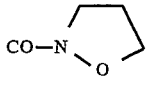 | OMe | OMe | CH | |
| 3.90 | H | Me | Me | 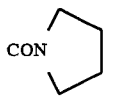 | OMe | OMe | CH | |

TABLE 3-continued

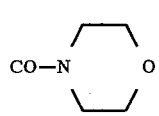

| Tab. Ex. | R¹ | R⁵ | R³ᵇ | R⁴ᵇ | X | Y | Z | m.p.(°C.) |
|---|---|---|---|---|---|---|---|---|
| 3.91 | H | Me | Me | CO—N⟨O⟩ | | OMe | OMe | CH |

TABLE 4

$$\text{R}^{3b}\text{R}^{4b}\text{N}-\bigcirc-\begin{array}{c}CO_2R^5\\SO_2-N-CO-NR^1\end{array}-\bigcirc\begin{array}{c}N\\N\end{array}\begin{array}{c}Y\\Z\\X\end{array}$$

| Tab. Ex. | R¹ | R⁵ | R³ᵇ | R⁴ᵇ | M | X | Y | Z | m.p.(°C.) |
|---|---|---|---|---|---|---|---|---|---|
| 4.1 | H | Me | Me | CO₂Me | Na | OMe | OMe | CH | 166 (Decomp.) |
| 4.2 | H | Me | Me | CO₂Me | K | OMe | OMe | CH | |
| 4.3 | H | Me | Me | CO₂Me | Na | OMe | Cl | CH | 134–5 (Decomp.) |
| 4.4 | H | Me | Me | CO₂Me | K | OMe | Cl | CH | |
| 4.5 | H | Me | Me | CO₂Me | NH₄ | OMe | OMe | CH | |
| 4.6 | H | Me | Me | CO₂Me | Na | OMe | Me | N | 170–3 (Decomp.) |
| 4.7 | H | Me | Me | CHO | Na | OMe | Me | N | |
| 4.8 | H | Me | Me | CHO | Na | OMe | OMe | CH | 149–53 (Decomp.) |
| 4.9 | H | Me | Me | CHO | K | OMe | OMe | CH | |
| 4.10 | H | Me | Me | CHO | K | OMe | Me | N | |
| 4.11 | H | Me | Me | COCH₃ | K | OMe | Me | N | |
| 4.12 | H | Me | Me | COCH₃ | K | OMe | OMe | CH | |
| 4.13 | H | Me | Me | COCH₃ | Na | OMe | OMe | CH | |
| 4.14 | H | Me | Me | CO₂Me | Na | OMe | OMe | N | 169–73 (Decomp.) |
| 4.15 | H | Me | Me | COCH₃ | Na | OMe | OMe | CH | 110–5 (Decomp.) |
| 4.16 | H | Me | Me | CONHEt | Na | OMe | OMe | CH | 160–3 (Decomp.) |

B. Formulation Examples a) A dusting agent is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of oxethylated nonylphenol as the emulsifier.

e) Water-dispersible granules are obtained by mixing 75 parts by weight of a compound of the formula (I), 10 parts by weight of calcium ligninsulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed, by spraying on water as the granulation fluid.

f) Water-dispersible granules are also obtained by homogenizing and precomminuting 25 parts by weight of a compound of the formula (I), 5 parts by weight of sodium2,2'-dinaphthylmethane-6,6'-disulfonate 2 parts by weight of sodium oleoylmethyltaurate, 1 part by weight of polyvinyl alcohol, 17 parts by weight of calcium carbonate and 50 parts by weight of water in a colloid mill, then grinding the mixture on a bead mill, atomizing the resulting suspension in a spray tower using a single-substance nozzle, and drying.

C. Biological Examples

1. Pre-emergence effect on weeds

Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the test results, the compounds according to the invention have a good herbicidal pre-emergence action against a broad range of gramineous and dicotyledon weeds. For example, the compounds of Examples 1.13, 1.14, 1.24, 2.1, 2.15, 2.69, 2.80. 2.81, 2.92, 2.101, 2.105, 2.106, 2.119–2.125, 4.1, 4.3, 4.6, 4.8, 4.14, 4.15 and 4.16 from Tables 1–4 have a very good herbicidal action against harmful plants such as *Sinapis alba, Chrysanthemum segetum, Avena sativa, Stellaria media, Echinochloa crus-galli* and *Lolium multiflorum* when applied pre-emergence at a rate of 0.3 kg or less active substance per hectare.

2. Post-emergence effect on weeds

Seeds or rhizome pieces of monocotyledon and dicotyledon weeds were placed in sandy loam soil in plastic pots, covered with soil and grown in a greenhouse under good growth conditions. Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls. The agents according to the invention also have a good herbicidal post-emergence action against a broad range of economically important gramineous and dicotyledon weeds. For example, the compounds of Examples 1.13, 1.14, 1.24, 2.1, 2.15, 2.69, 2.80. 2.81, 2.92, 2.101, 2.105, 2.106, 2.119–2.125, 4.1, 4.3, 4.6, 4.8, 4.14, 4.15 and 4.16 from Tables 1–4 have a very good herbicidal action against harmful plants such as *Sinapis alba, Stellaria media, Echinochloa crus-galli, Lolium multiflorum, Chrysanthemum segetum* and *Avena sativa* when applied post-emergence at a rate of 0.3 kg or less active substance per hectare.

3. Tolerance by crop plants

In further greenhouse experiments, seeds of a substantial number of crop plants and weeds were placed in sandy loam soil and covered with soil. Some of the pots were treated immediately as described under section 1, and the remaining pots were placed in a greenhouse until the plants had developed two to three leaves and then sprayed with various dosages of the substances of the formula (I) according to the invention, as described under section 2. Visual scoring four to five weeks after the application and after the plants had been in the greenhouse revealed that the compounds according to the invention did not inflict any damage on dicotyledon crops such as, for example, soya, cotton, oilseed rape, sugar beet and potatoes when used pre- and post-emergence, even when high dosages of active substance were used. Moreover, some substances also left Gramincas crops such as, for example, barley, wheat, rye, Sorghum species, maize or rice unharmed. The compounds of the formula (I) therefore have a high selectivity when used for combating unwanted plant growth in agricultural crops.

We claim:

1. A compound of the formula (I) or a salt thereof

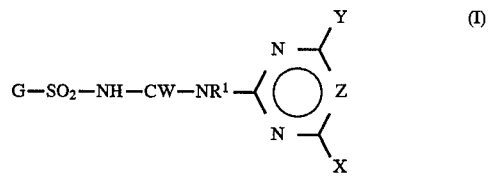

in which

G is a substituted N-acylaminophenyl radical from the group consisting of $G^1$, and $G^3$

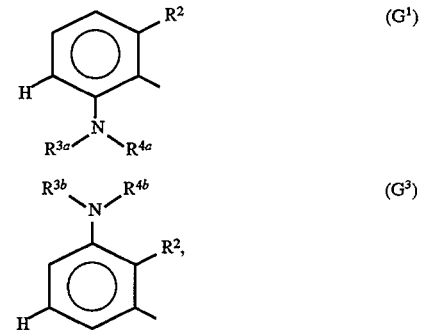

$R^1$ is H or alkyl, $R^2$ is carboxyl, thiocarboxyl or a derivative of the carboxyl or thiocarboxyl group of 1 to 20 carbon atoms, or is acyl of the type CO-R° of 1 to 12 carbon atoms, in which R° is hydrogen or a saturated or unsaturated, and acyclic or cyclic aliphatic radical, or is an imine, hydrazone or oxime derivative of the group CO-R°, $R^{3a}$ is hydrogen or a hydrocarbon radical which is unsubstituted or substituted and is of 1 to 18 carbon atoms in total, $R^{3b}$ is hydrogen or a hydrocarbon radical which is un. substituted or substituted and is of 1 to 18 carbon atoms in total, $R^{4a}$ is alkylcarbonyl or alkoxycarbonyl of 2 to 12 carbon atoms, the two latter radicals being unsubstituted or substituted by one or more radicals from the group consisting of hydroxyl, amino, substituted amino, azido, cyano, carboxyl, ($C_1$–$C_4$-alkoxy) carbonyl and ($C_1$–$C_4$-alkyl)thio, -sulfinyl and -sulfonyl, or is aminocarbonyl or aminosulfonyl, the two latter radicals being unsubstituted, N-monosubstituted or N,N-disubstituted, $R^{4b}$ is formyl or aliphatic acyl from the group consisting of CO-R, CS-R, CO-OR, CS-OR and CS-SR of 2 to 12 carbon atoms, R'SO or R'SO$_2$, in which R and R' are each a hydrocarbon radical which is unsubstituted or substituted, or is aminocarbonyl or aminosulfonyl, the two latter radicals being unsubstituted, N-monosubstituted or N,N-disubstituted, W is an oxygen or sulfur atom,

37

X and Y independently of one another are hydrogen, halogen, $C_1$–$C_4$-alkyl, $C_1$–$C_4$-alkoxy or $C_1$–$C_4$-alkylthio, the three latter radicals being unsubstituted or substituted by one or more radicals from the group consisting of halogen, $C_1$–$C_4$-alkoxy and $C_1$–$C_4$-alkylthio or are mono- or di-($C_1$–$C_4$-alkyl)amino, $C_3$–$C_6$-cycloalkyl, $C_3$–$C_5$-alkenyl, $C_3$–$C_5$-alkenyloxy or $C_3$–$C_5$-alkynyloxy, and Z is CH or N.

2. A compound or salt thereof as claimed in claim 1, wherein $R^1$ is H or $C_1$–$C_3$-alkyl, $R^2$ is CO-$OR^5$, CS-$SR^6$, CO-$SR^7$, CS-$OR^8$, CO-$R^9$, CO-$NR^{10}R^{11}$, CO-O-N=$CR^{12}R^{13}$, C(=$NR^{14}$) $R^{15}$ or CS-$NR^{16}R^{17}$, $R^{3a}$ is H, $C_1$–$C_5$-alkyl, $C_2$–$C_5$-alkenyl or $C_2$–$C_5$-alkynyl, the three latter radicals being unsubstituted or substituted by one or more radicals from the group consisting of halogen, $C_1$–$C_4$-alkoxy, CN, di-($C_1$–$C_4$-alkyl) amino, $N_3$, and $C_1$–$C_3$-alkylthio, $R^{3b}$ is H, $C_1$–$C_5$-alkyl, $C_3$–$C_6$-cycloalkyl, or $C_2$–$C_5$-alkenyl or $C_2$–$C_5$-alkynyl, the four latter radicals being unsubstituted or substituted by one or more radicals from the group consisting of halogen, $C_1$–$C_4$-alkoxy, CN, di-($C_1$–$C_4$-alkyl) amino, $N_3$ and $C_1$–$C_3$-alkylthio, $R^{4a}$ is CO- ($C_1$–$C_5$-alkyl) or $CO_2$- ($C_1$–$C_5$-alkyl), the two latter radicals being unsubstituted or substituted by one or more radicals from the group consisting of OH, $NR^{18}R^{19}$, $N_3$, CN, $CO_2H$, $S(O)_x$-($C_1$–$C_4$-alkyl) and $CO_2$-($C_1$–$C_3$-alkyl) , or is aminocarbonyl or aminosulfonyl, the two latter radicals being unsubstituted or N-substituted by identical or different radicals from the group consisting of $C_1$–$C_4$-alkyl and $C_1$–$C_4$-haloalkyl, $R^{4b}$ is CHO, CO- ($C_1$–$C_5$-alkyl), CO-($C_3$–$C_6$-cycloalkyl), $CO_2$- ($C_1$–$C_5$-alkyl), CO-($C_2$–$C_5$-alkenyl), CS-($C_1$–$C_5$-alkyl), CO-($C_2$–$C_5$-alkynyl), CO-S-($C_1$–$C_6$-alkyl), CS-O-($C_1$–$C_6$-alkyl) or CS-S-($C_1$–$C_6$-alkyl), the nine latter radicals being unsubstituted or substituted by one or more radicals from the group consisting of halogen, CN, $N_3$, $CO_2H$, $CO_2$-($C_1$–$C_3$-alkyl), OH, $NR^{20}R^{21}$, $S(O)_x$-($C_1$–$C_4$-alkyl), CO-$NR^{22}R^{23}$ and $C_1$–$C_3$-alkoxy, or is CO-$NR^{24}R^{25}$, CS-$NR^{26}R^{27}$, $SO_2R^{28}$ or $SO_2NR^{29}R^{30}$, $R^5$ is $C_1$–$C_5$-alkyl, $C_2$–$C_5$-alkenyl, $C_2$–$C_5$-alkynyl, $C_3$–$C_6$-cycloalkyl or $C_4$–$C_7$-cycloalkylalkyl, the latter five radicals being unsubstituted or substituted by one or more radicals from the group consisting of halogen, CN, $N_3$, $C_1$–$C_3$-alkoxy, $C_1$–$C_3$-alkylthio, amino, mono- and di-($C_1$–$C_4$-alkyl)amino, $NO_2$, SCN, $C_1$–$C_3$-haloalkoxy and $C_1$–$C_3$-haloalkylthio, $R^6$ is a radical as for $R^5$, $R^7$ is a radical as for $R^5$, $R^8$ is a radical for $R^5$, $R^9$ is H, $C_1$–$C_6$-alkyl, $C_2$–$C_6$-alkenyl, $C_2$–$C_6$-alkynyl, $C_3$–$C_7$-cycloalkyl, the four latter radicals independently of one another being unsubstituted or substituted by one or more radicals from the group consisting of halogen, $C_1$–$C_4$-alkoxy, $C_1$–$C_4$-alkylythio, $C_1$–$C_4$-haloalkoxy, $C_1$–$C_4$-haloalkylthio and CN, $R^{10}$ is H, $C_1$–$C_6$-alkyl, $C_2$–$C_6$-alkenyl, $C_2$–$C_6$-alkynyl, the three latter radicals being unsubstituted or substituted by one or more radicals from the group consisting of $C_1$–$C_3$-alkoxy, $C_1$–$C_3$-alkylthio, halogen, CN, amino $C_1$–$C_4$-alkylamino and di-($C_1$–$C_4$-alkyl)amino, or is $C_1$–$C_4$-alkoxy or OH,

38

$R^{11}$ is H, $C_1$–$C_6$-alkyl, $C_2$–$C_6$-alkenyl, $C_2$–$C_6$-alkynyl, the three latter radicals being unsubstituted or substituted by one or more radicals from the group consisting of halogen, CN, $NH_2$, mono- and di-($C_1$–$C_4$-alkyl)amino, $C_1$–$C_3$-alkoxy and $C_1$–$C_3$-alkylthio, or $NR^{10}R^{11}$ together is a heterocyclic ring which is selected from the group consisting of 1-piperidyl, 1-piperazinyl, 4-morpholinyl, 1-pyrrolidinyl, 1-oxa-3-aza-cyclopent-3-yl and 1-oxa-2-aza-cyclopent-3-yl, which is unsubstituted or is substituted, $R^{12}$ and $R^{13}$ independently of one another are H, $C_1$–$C_4$-alkyl, $C_2$–$C_4$-alkenyl or $C_2$–$C_4$-alkynyl, or $R^{12}$ and $R^{13}$ together are an alkylene chain of 3 or 4 carbon atoms, which may also be substituted by $C_1$–$C_4$-alkyl or $C_1$–$C_4$-alkoxy, $R^{14}$ is H, OH, NH2, $NHR^{31}$, $NR^{31}{}_2$, $C_1$–$C_4$-alkyl, $C_1$–$C_4$-alkoxy, $C_2$–$C_4$-alkenyl or $C_2$–$C_4$-alkynyl, the four latter radicals being unsubstituted or substituted by one or more radicals from the group consisting of halogen, $C_1$–$C_3$-alkoxy and $C_1$–$C_3$-alkylthio, $R^{15}$ is H, $C_1$–$C_6$-alkyl, $C_1$–$C_6$-alkoxy, $C_2$–$C_6$-alkenyl, $C_2$–$C_6$-alkynyl, the four latter radicals being unsubstituted or substituted by one or more radicals from the group consisting of halogen, $C_1$–$C_3$-alkoxy and $C_1$–$C_3$-alkylthio, $R^{16}$ is a radical as for $R^{10}$, $R^{17}$ is a radical as for $R^{11}$, $R^{18}$ independently of $R^{19}$ is H, $C_1$–$C_4$-alkyl, $C_2$–$C_5$-alkenyl or $C_2$–$C_5$-alkynyl, the three latter radicals being unsubstituted or substituted by one or more radicals from the group consisting of halogen, $C_1$–$C_3$-alkoxy, $C_1$–$C_3$-alkylthio and CN, $R^{19}$ independently of $R^{18}$ is a radical as for $R^{18}$ or is $C_1$–$C_3$-alkoxy or OH, or $NR^{18}R^{19}$ is a heterocyclic ring of the formula K1 to K5,

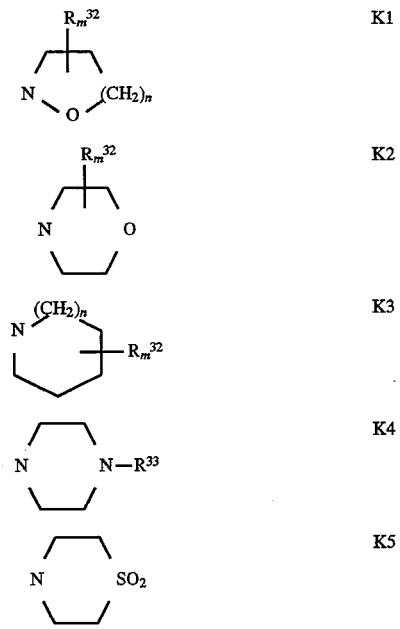

$R^{20}$ independently of $R^{21}$ is H, $C_1$–$C_4$-alkyl, $C_2$–$C_4$-alkenyl or $C_2$–$C_4$-alkynyl, the three latter radicals being unsubstituted or substituted by one or more radicals from the group consisting of halogen, CN, $NH_2$, mono- and di ($C_1C_4$) alkylamino, $C_1$–$C_3$-alkoxy, $C_1$–$C_3$-alkylthio and $CO_2$-($C_1$–$C_3$-alkyl), $R^{21}$ independently of $R^{20}$ is a radical as for $R^{20}$ or is CHO, CO-($C_1$-$C_5$-alkyl) or $CO_2$-($C_1$-$C_5$-alkyl) or $NR^{20}R^{21}$ is a heterocyclic ring as in $NR^{18}R^{19}$, $R^{22}$ and $R^{23}$ independently of one another are H, $C_1$-$C_3$alkyl, $C_2$-$C_4$-alkenyl, $C_2$-$C_4$-alkynyl or $NR^{22}R^{23}$ is a heterocyclic ring as in $NR^{18}R^{19}$, $R^{24}$ independently of $R^{25}$ is H, $C_1$-$C_4$-alkyl, $C_2$-$C_5$-alkenyl or $C_2$-$C_5$-alkynyl, the three latter radicals being unsubstituted or substituted by one or more radicals from the group consisting of halogen, $C_1$-$C_3$-alkoxy, $C_1$-$C_3$-alkylthio and CN, $R^{25}$ independently of $R^{24}$ is H, $C_1$-$C_4$-alkyl, $C_2$-$C_5$-alkenyl or $C_2$-$C_5$-alkynyl, the three latter radicals being unsubstituted or substituted by one or more radicals from the group consisting of halogen, $C_1$-$C_3$-alkoxy, $C_1$-$C_3$-alkylthio and CN, or is $C_1$-$C_3$-alkoxy or OH, or $NR^{24}R^{25}$ is a heterocyclic ring as in $NR^{18}R^{19}$, $R^{26}$ independently of $R^{27}$ is a radical as for $R^{24}$, $R^{27}$ independently of $R^{26}$ is a radical as for $R^{26}$ or is $C_1$-$C_3$-alkoxy or OH, or $NR^{26}R^{27}$ is a heterocyclic ring as in $NR^{18}R^{19}$, $R^{28}$ is $C_1$-$C_5$-alkyl, $C_2$-$C_5$-alkenyl or $C_2$-$C_5$-alkynyl, the three latter radicals being unsubstituted or substituted by one or more radicals from the group consisting of halogen, CN, $C_1$-$C_3$-alkoxy and $C_1$-$C_3$-alkylmercapto, independently of $R^{30}$ is a radical as for $R^{24}$, $R^{30}$ independently of $R^{29}$ is a radical as for $R^{25}$ or $NR^{29}R^{30}$ is a heterocyclic ring as in $NR^{18}R^{19}$, $R^{31}$ is $C_1$-$C_4$-alkyl, $C_2$-$C_4$-alkenyl or $C_2$-$C_4$-alkynyl, the three latter radicals independently of one another being unsubstituted or substituted by one or more radicals from the group consisting of halogen, $C_1$-$C_4$-alkoxy and $C_1$-$C_4$-alkylthio, $R^{32}$ is H, $C_1$-$C_3$-alkyl, $C_1$-$C_3$-haloalkyl, $C_1$-$C_3$-alkoxyalkyl, halogen or CN, $R^{33}$ is H, $C_1$-$C_3$-alkyl, $C_2$-$C_4$-alkenyl or $C_2$-$C_4$-alkynyl, the three latter radicals being unsubstituted or substituted by a radical from the group consisting of halogen, $C_1$-$C_4$-alkoxy, CN and $C_1$-$C_4$-alkylthio, n is 1, 2, 3, or 4, m is 1 or 2, x—independently of the other indices x—is 0, 1 or 2, w is O or S, and X and Y independently of one another are hydrogen, halogen, $C_1$-$C_1$-alkyl, $C_1$-$C_2$-alkoxy or $C_1$-$C_2$-alkylthio, the three latter radicals being unsubstituted or substituted by one or more radicals from the group consisting of halogen, $C_1$-$C_2$-alkoxy and $C_1$-$C_2$-alkylthio, or are mono- or di-($C_1$-$C_2$-alkyl) amino, $C_3$-$C_4$-alkenyl, $C_3$-$C_4$-alkenyloxy or $C_3$-$C_4$-alkynyloxy, and Z is CH.

3. A compound or salt thereof as claimed in claim 1, wherein

G is a radical of the formula (G1) and $R^1$ is H or $C_1$-$C_3$-alkyl, $R^2$ is CO-$OR^5$, CS-$SR^6$, CO-$SR^7$, CS-$OR^8$, CO-$R^9$, CO-$NR^{10}R^{11}$, CO-O-N=$CR^{12}R^{13}$, C(=$NR^{14}$)$R^{15}$ or CS-$NR^{16}R^{17}$, $R^{3a}$ is H, $C_1$-$C_4$-alkyl, $C_1$-$C_4$-haloalkyl, $C_2$-$C_4$-alkenyl or $C_2$-$C_4$-alkynyl, $R^{4a}$ is CO-($C_1$-$C_4$-alkyl), $CO_2$-($C_1$-$C_5$-alkyl) or CO-$NH_2$, CO-NH($C_1$-$C_4$-alkyl), CO-N($C_1$-$C_4$-alkyl)$_2$ or $SO_2$-$NH_2$, $SO_2$-NH($C_1$-$C_4$-alkyl) or $SO_2$-N($C_1$-$C_4$-alkyl)$_2$, $R^5$ is $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl or $C_4$-$C_7$-cycloalkylmethyl, $R^6$ is a radical as for $R^5$, $R^7$ is a radical as for $R^5$, $R^8$ is a radical as for $R^5$, $R^9$ is H, $C_1$-$C_4$-alkyl, $C_2$-$C_4$-alkenyl, $C_2$-$C_4$-alkynyl or $C_3$-$C_6$-cycloalkyl, the four latter radicals independently of one another being unsubstituted or substituted by one or more radicals from the group consisting of halogen, $C_1$-$C_2$-alkoxy, $C_1$-$C_2$-alkylthio, $C_1$-$C_2$-haloalkoxy, $C_1$-$C_2$-haloalkylthio and CN, $R^{10}$ and $R^{11}$ independently of one another are H, $C_1$-$C_4$-alkyl, $C_2$-$C_4$-alkenyl or $C_2$-$C_4$-alkynyl, $R^{12}$ and $R^{13}$ independently of one another are H, $C_1$-$C_4$-alkyl, $C_2$-$C_4$-alkenyl or $C_2$-$C_4$-alkynyl or $R^{12}$ and $R^{13}$ together are an alkylene chain of 3 or 4 carbon atoms, which may also be substituted by $C_1$-$C_4$-alkyl or $C_1$-$C_4$-alkoxy, $R^{14}$ is $NH_2$, $NHR^{31}$, $NR^{31}{}_2$, $C_1$-$C_4$-alkyl, $C_1$-$C_4$-alkoxy, $C_2$-$C_4$-alkenyl or $C_2$-$C_4$-alkynyl, $R^{15}$ is H, $C_1$-$C_4$-alkyl, $C_1$-$C_4$-alkoxyl, or $C_2$-$C_4$-alkenyl $R^{16}$ is a radical as for $R^{10}$, $R^{17}$ is a radical as for $R^{11}$, $R^{31}$ is $C_1$-$C_4$-alkyl, $C_2$-$C_4$-alkenyl or $C_2$-$C_4$-alkynyl, W is O or S, X and Y independently of one another are halogen, $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, mono- or di-($C_1$-$C_2$-alkyl) amino, $C_3$-$C_4$-alkenyl, $C_3$-$C_4$-alkenyloxy or $C_3$-$C_4$-alkynyloxy; and Z is CH.

4. A compound or salt thereof as claimed in claim 1, wherein

G is a radical of the formula (G3), and $R^1$ is H or $C_1$-$C_3$-alkyl, $R^2$ is CO-$OR^5$, CS-$SR^6$, CO-$SR^7$, CS-$OR^8$, CO-$R^9$, CO-$NR^{10}R^{11}$, CO-O-N=$CR^{12}R^{13}$, C(=$NR^{14}$)$R^{15}$ or CS-$NR^{16}R^{17}$, $R^{3b}$ is H, $C_1$-$C_4$-alkyl, $C_3$-$C_6$-cycloalkyl, $C_1$-$C_4$-haloalkyl, $C_2$-$C_4$-alkenyl or $C_2$-$C_4$-alkynyl, $R^{4b}$ is CHO, CO-($C_1$-$C_4$-alkyl) , CO-($C_3$-$C_6$-cycloalkyl) or $CO_2$-($C_1$-$C_4$-alkyl), CO-($C_2$-$C_4$-alkenyl) or CO-($C_2$-$C_4$-alkynyl), the 5 latter radicals being unsubstituted or substituted by one or more radicals from the group consisting of halogen, CN, $NR^{20}R^{21}$, $S(O)_x$-($C_1$-$C_4$-alkyl, CO-$NR^{22}R^{23}$ and $C_1$-$C_3$-alkoxy, or is CO-$NR^{24}R^{25}$, $SO_2R^{28}$ or $SO_2NR^{29}R^{30}$, $R^5$ is $C_1$-$C_4$-alkyl, $C_2$-$C_4$-alkenyl, $C_2$-$C_4$-alkynyl, $C_3$-$C_6$-cycloalkyl or $C_4$-$C_7$-cycloalkylmethyl, the five latter radicals being unsubstituted or substituted by one or more radicals from the group consisting of halogen, $C_1$-$C_2$-alkoxy and $C_1$-$C_2$-haloalkoxyl, $R^6$ is a radical as for $R^5$, $R^7$ is a radical as for $R^5$, $R^8$ is a radical as for $R^5$, $R^9$ is H, $C_1$-$C_4$-alkyl, $C_2$-$C_4$-alkenyl, $C_2$-$C_4$-alkynyl or $C_3$-$C_6$-cycloalkyl, the four latter radicals independently of one another being unsubstituted or substituted by one or more radicals from the group consisting of halogen, $C_1$-$C_2$-alkoxy, $C_1$-$C_2$-alkylthio, $C_1$-$C_2$-haloalkoxy, $C_1$-$C_2$-haloalkylthio and CN, $R^{10}$ and $R^{11}$ independently of one another are H, $C_1$–$C_4$-alkyl, $C_2$–$C_4$-alkenyl or $C_2$–$C_4$-alkynyl, $R^{12}$ and $R^{13}$ independently of one another are H, $C_1$–$C_4$-alkyl, $C_2$–$C_4$-alkenyl, or $C_2$–$C_4$-alkynyl, or $R^{12}$ and $R^{13}$ together are an alkylene chain of 3 or 4 carbon atoms, which may also be substituted by $C_1$–$C_4$-alkyl or $C_1$–$C_4$-alkoxy, $R^{14}$ is $NH_2$, $NHR^{31}$, $NR^{31}{}_2$, $C_1$–$C_4$-alkyl, $C_1$–$C_4$-alkoxy, $C_2$–$C_4$-alkenyl or $C_2$–$C_4$-alkynyl, $R^{15}$ is H, $C_1$–$C_4$-alkyl, $C_1$–$C_4$-alkoxy, $C_2$–$C_4$-alkenyl or $C_2$–$C_4$-alkynyl, $R^{16}$ is a radical as for $R^{10}$ $R^{17}$ is a radical as for $R^{11}$, $R^{20}$ independently of $R^{21}$ is H, $C_1$–$C_4$-alkyl, $C_2$–$C_4$-alkenyl or $C_2$–$C_4$-alkynyl, the three latter radicals being unsubstituted or substituted by one or more radicals from the group consisting of halogen and $C_1$–$C_2$-alkoxy, $R^{21}$ independently of $R^{20}$ is a radical as for $R^{20}$ or is CHO, CO-($C_1$–$C_4$-alkyl) or $CO_2$-($C_1$–$C_4$-alkyl) or $NR^{20}R^{21}$ is a heterocyclic ring of the formula K1 to K5

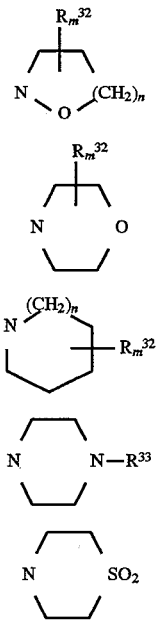

$R^{22}$ and $R^{23}$ independently of one another are H, $C_1$–$C_3$-alkyl, $C_2$–$C_4$-alkenyl or $C_2$–$C_4$-alkynyl or $NR^{22}R^{23}$ is a heterocyclic ring as in $NR^{20}R^{21}$, $R^{24}$ independently of $R^{25}$ is H, $C_1$–$C_4$-alkyl, $C_2$–$C_4$-alkenyl or $C_2$–$C_4$-alkynyl, the three latter radicals being unsubstituted or substituted by one or more radicals from the group consisting of halogen, $C_1$–$C_3$-alkoxy, $C_1$–$C_3$-alkylthio and CN, $R^{25}$ independently of $R^{24}$ is H, $C_1$–$C_4$-alkyl, $C_2$–$C_4$-alkenyl or $C_2$–$C_4$-alkynyl, the three latter radicals being unsubstituted or substituted by one or more radicals from the group consisting of halogen, $C_1$–$C_3$-alkoxy, $C_1$–$C_3$-alkylthio and CN, or is $C_1$–$C_3$-alkoxy or OH, or $NR^{24}R^{25}$ is a heterocyclic ring as in $NR^{20}R^{21}$, $R^{28}$ is $C_1$–$C_4$-alkyl, $C_2$–$C_4$-alkenyl or $C_2$–$C_4$-alkynyl, the three latter radicals being unsubstituted or substituted by one or more radicals from the group consisting of halogen and $C_1$–$C_2$-alkoxy, $R^{29}$ independently of $R^{30}$ is a radical as for $R^{24}$ $R^{30}$ independently of $R^{29}$ is a radical as for $R^{25}$, or $NR^{29}R^{30}$ is a heterocyclic ring as in $NR^{20}R^{21}$, $R^{31}$ is $C_1$–$C_4$-alkyl, $C_2$–$C_4$-alkenyl or $C_2$–$C_4$-alkynyl, x is 0, 1 or 2

W is O or S,

X and Y independently of one another are halogen, $C_1$–$C_2$-alkyl, $C_1$–$C_2$-haloalkyl, $C_1$–$C_2$-alkoxy, $C_1$–$C_2$-haloalkoxy, $C_1$–$C_2$-alkylthio, mono- or di-($C_1$–$C_2$-alkyl)amino, $C_3$–$C_4$-alkenyl, $C_3$–$C_4$-alkenyloxy or $C_3$–$C_4$-alkynyloxy; and Z is CH.

5. A compound of the formula (I) as claimed in claim wherein

G is a radical of the formula ($G^1$), $R^1$ is H or methyl, $R^2$ is CO-$OR^5$, $R^{3a}$ is H or $C_1$–$C_4$-alkyl, $R^{4a}$ is CO-($C_1$–$C_4$ alkyl) or $CO_2$-($C_1$–$C_4$-alkyl), $R^5$ is $C_1$–$C_4$-alkyl, X is methyl, ethyl, methoxy, ethoxy or chloro, Y methyl, ethyl, methoxy or ethoxy and Z is CH.

6. A compound of the formula (I) as claimed in claim 5 wherein $R^1$ is H, $R^2$ is CO-$OR^5$, $R^{3a}$ is $C_1$–$C_4$-alkyl, $R^{4a}$ is CO-($C_1$–$C_4$-alkyl) or $CO_2$-($C_1$–$C_4$-alkyl), and $R^5$ is methyl or ethyl.

7. A compound of the formula (I) as claimed in claim 6 wherein $R^2$ is CO-$OR^5$, $R^{3a}$ is methyl, $R^{4a}$ is $CO_2$-$CH_3$, and $R^5$ is methyl.

8. A herbicidal or plant growth-regulatory composition which comprises one or more compounds of the formula (I) or salt thereof as claimed in claim 1 and an inert carrier.

9. A method of combating harmful plants or for controlling the growth of plants wherein an effective amount of a compound of the formula (I) as claimed in claim 1 is used as a herbicide or plant growth regulator, respectively.

10. A method as claimed in claim 9, which comprises applying the one or more compounds of the formula (I) to the plants, plant seed or the soil on or in which the plants are growing.

* * * * *